United States Patent [19]

Ciccone et al.

[11] Patent Number: 4,952,289
[45] Date of Patent: Aug. 28, 1990

[54] MACROCYCLIC AMINE COMPLEXES FOR LIGAND EXTRACTION AND GENERATION

[75] Inventors: Joseph P. Ciccone, Davis; Emory S. DeCastro, Emeryville; John B. Kerr, Oakland, all of Calif.

[73] Assignee: Aquanautics Corporation, Alameda, Calif.

[21] Appl. No.: 191,519

[22] Filed: May 9, 1988

[51] Int. Cl.$^5$ .............................................. C25B 1/02
[52] U.S. Cl. .................... 204/129; 204/130; 204/182.3; 204/233; 204/235; 423/219; 423/579; 544/4; 544/7; 544/64; 544/66; 546/2; 548/101; 548/108; 548/109; 548/402; 556/14; 556/16; 556/45; 556/49; 556/50; 556/110; 556/113; 556/146
[58] Field of Search ................... 204/129, 130, 180.1, 204/182.3, 182.5, 233, 235, 252, 263, 266; 261/161, DIG. 28; 422/48; 423/219, 579; 544/4, 66, 7, 64; 546/2; 548/101, 108, 109, 402; 556/13, 14, 16, 42, 44, 45, 49, 50, 110, 113, 146, 138

[56] References Cited

U.S. PATENT DOCUMENTS

| | | | |
|---|---|---|---|
| 4,474,963 | 10/1984 | Gokel | 546/178 |
| 4,577,042 | 3/1986 | Collins et al. | 564/158 |
| 4,602,987 | 7/1986 | Bonaventura et al. | 204/129 |

FOREIGN PATENT DOCUMENTS

| | | |
|---|---|---|
| 88/002036 | 3/1988 | World Int. Prop. O. |
| 88/006641 | 9/1988 | World Int. Prop. O. |

Primary Examiner—John F. Niebling
Assistant Examiner—Kathryn Gorgos
Attorney, Agent, or Firm—Townsend and Townsend

[57] ABSTRACT

Methods and apparatus for electrochemical extraction of a ligand such as molecular oxygen from a first fluid environment and for release of a ligand such as molecular oxygen, as well as ligand carrier compounds therefor comprising macrocyclic amines having the general formulas:

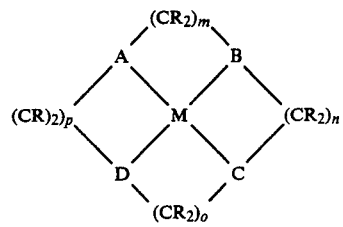

and:

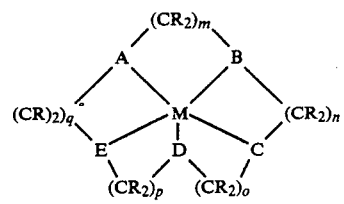

and:

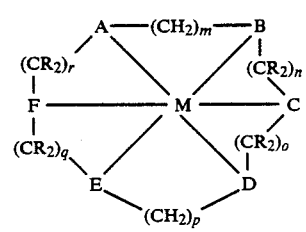

where:
A, B, C, D, E, and F are each nitrogen, oxygen, sulfur, or phosphorous;
m, n, o, p, q, and r are each typically 2, 3, 4, 5, or 6;
the R substituents are each generally H or short chain (linear or branched) alkyl, although $R_2$ may represent ketyl (=o); and
M is a suitable transition metal ion.

20 Claims, 6 Drawing Sheets

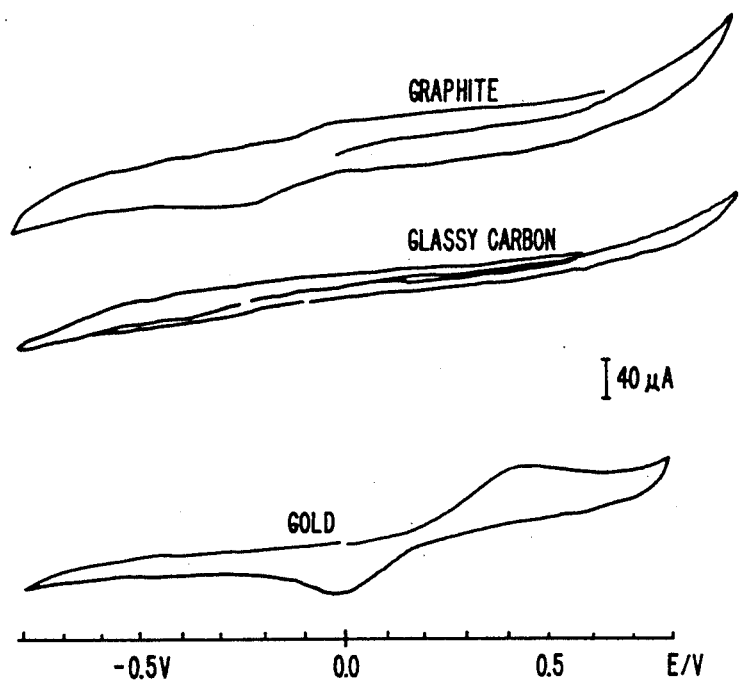
FIG._1A.
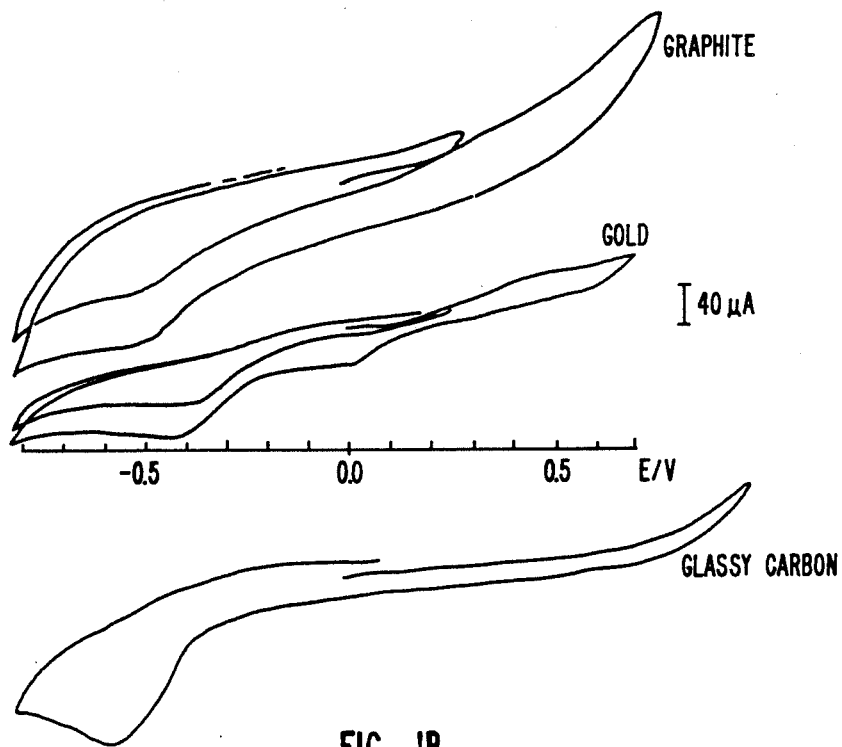
FIG._1B.

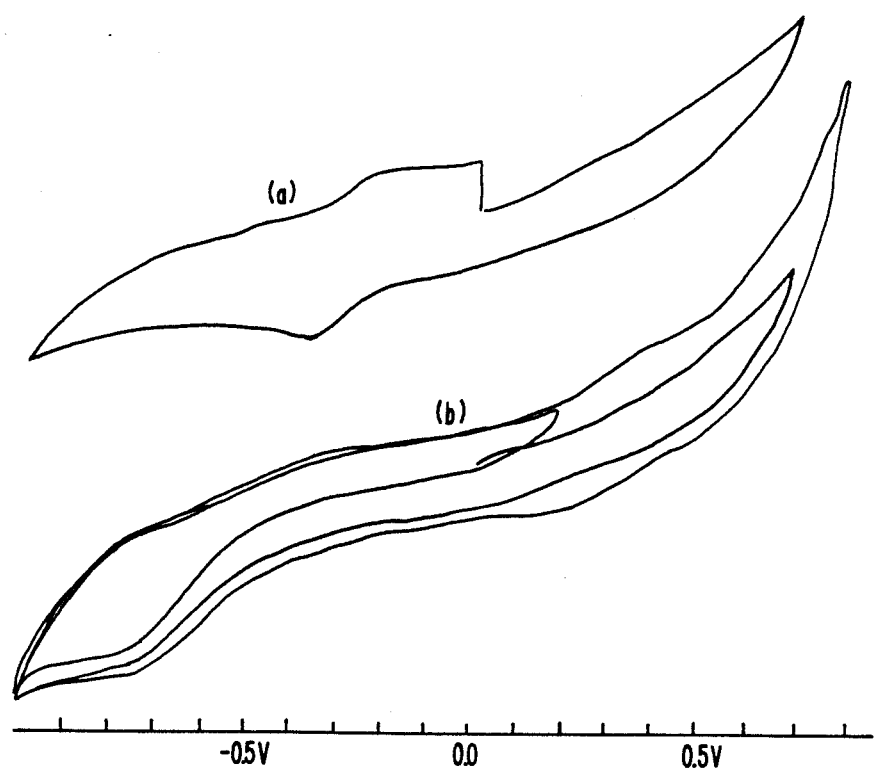
FIG._1C.
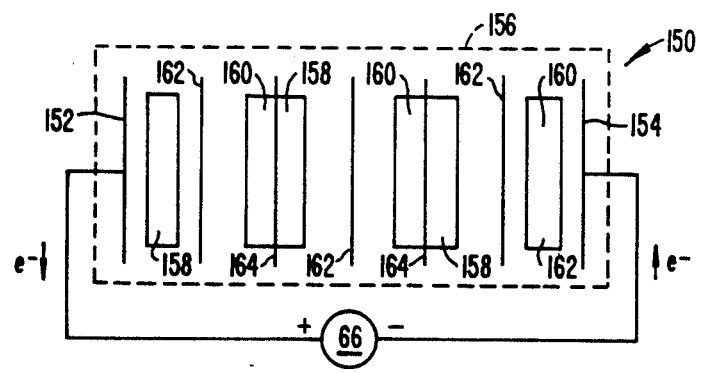
FIG._7.

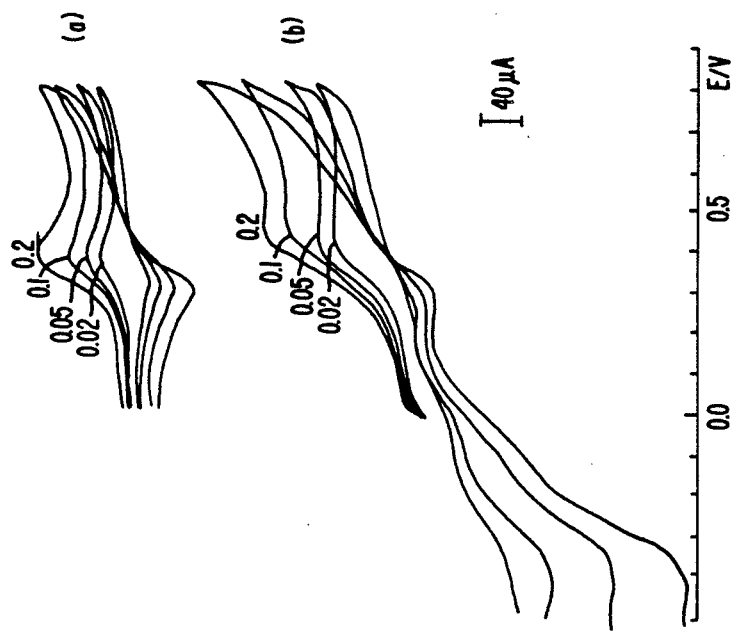
FIG._2A.
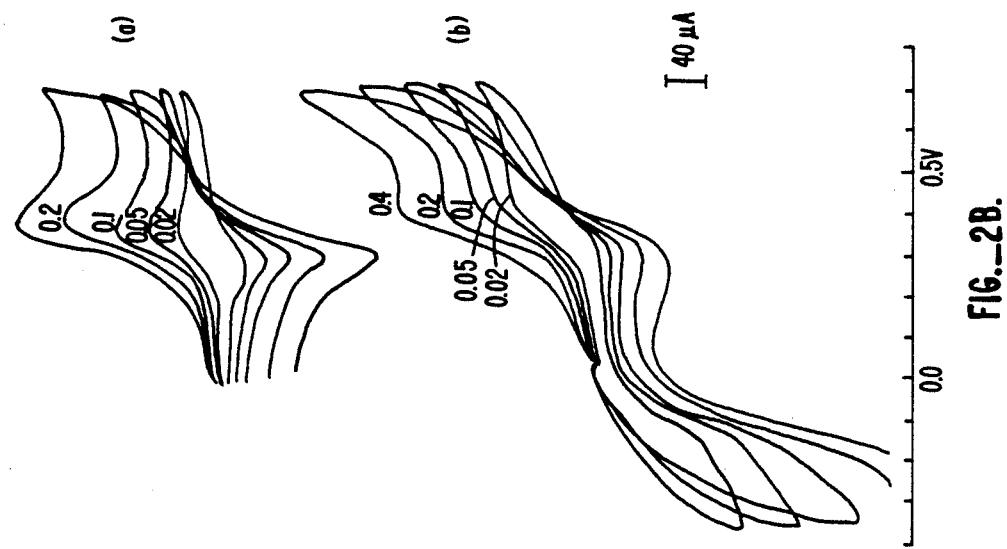
FIG._2B.

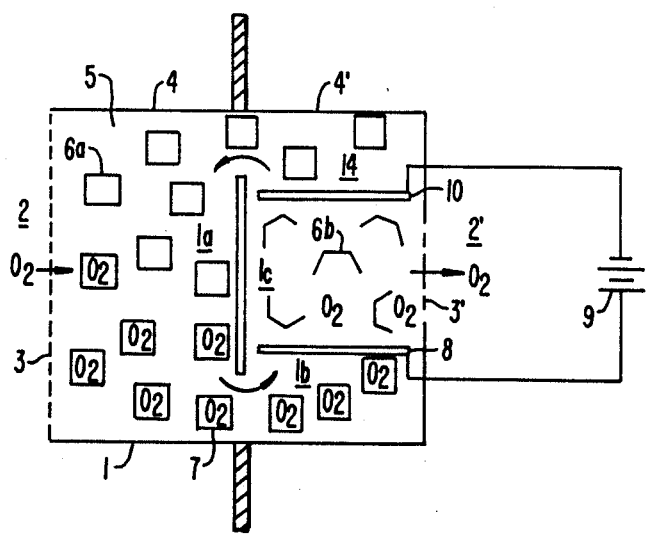
FIG._3.
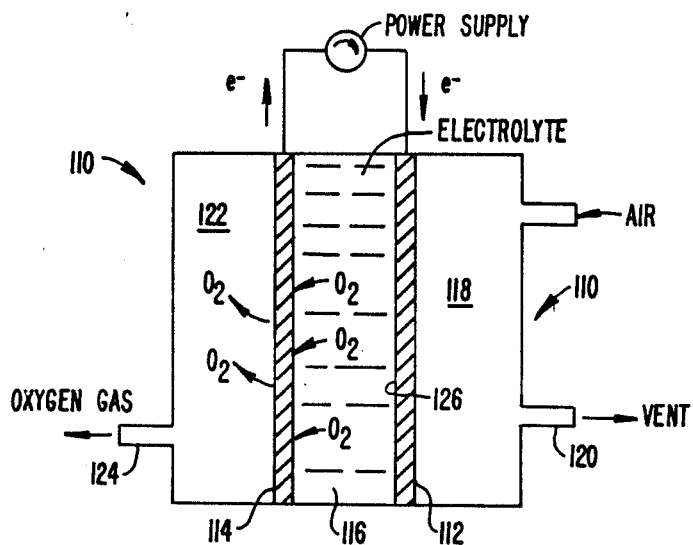
FIG._6.

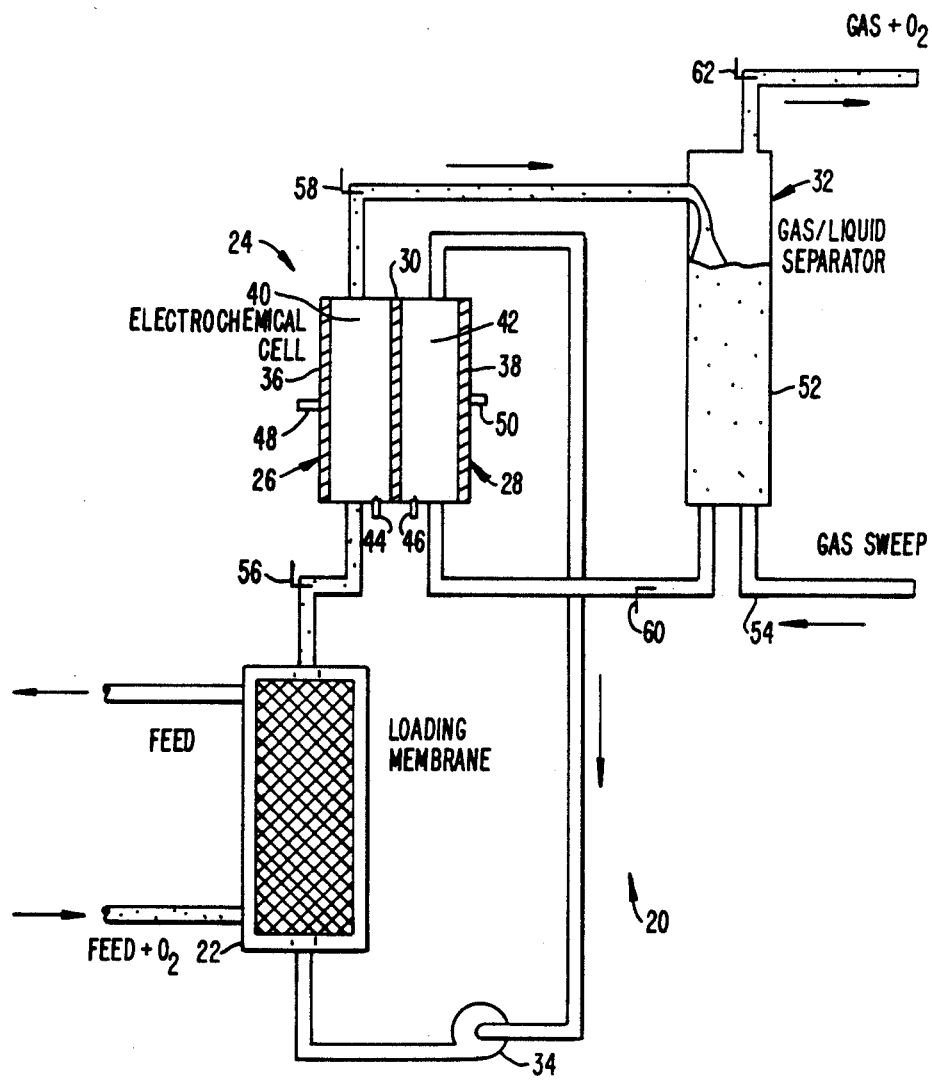
FIG._4.

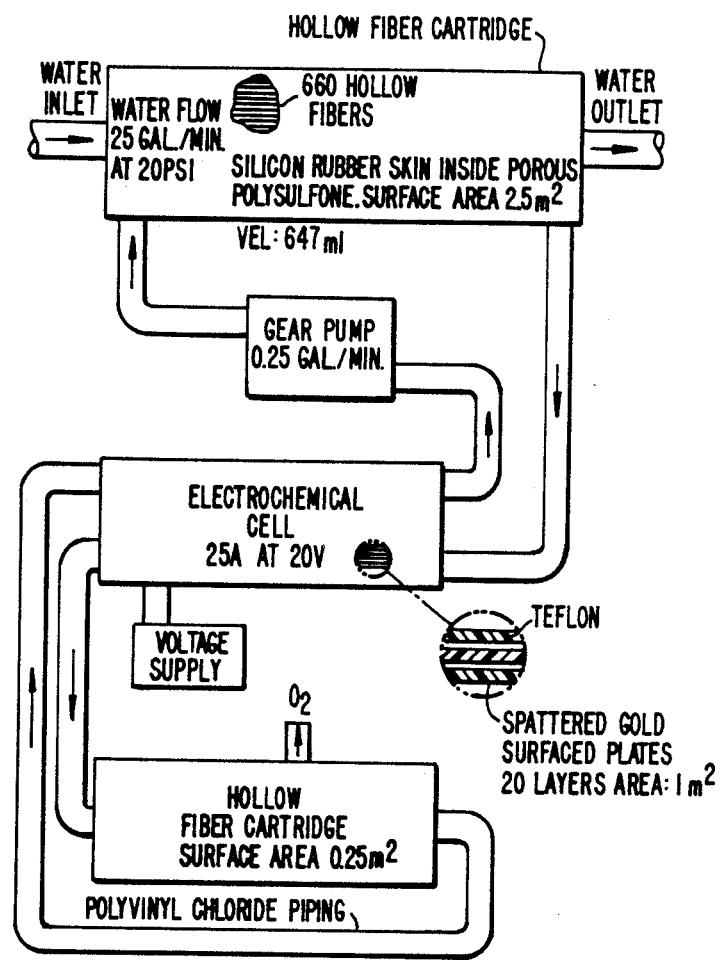
FIG._5.

MACROCYCLIC AMINE COMPLEXES FOR LIGAND EXTRACTION AND GENERATION

BACKGROUND OF THE INVENTION

1. Field of the Invention

This invention relates to carrier complexes for use in apparatus and methods for extracting small ligands from a fluid; more particularly, the invention relates to electrochemically active macrocyclic polyamine (also referred to as macrocyclic amine) complexes of transition metals that reversibly bind small ligands such as molecular oxygen and the use of such complexes for extraction of ligands from a first fluid environment and release ligands to a second fluid environment.

Purified gases, such as oxygen, are useful in a number of industrial, scientific and medical applications. Such gases may be obtained in a variety of ways. Large-scale extraction of gases from air may be accomplished by cryogenic fractionalization where the air is liquified and separated based on the differing boiling points of its constituent gases. Although practical for producing large volumes of gases, cryogenic fractional distillation is impractical for supplying small gas volumes, particularly at remote or inaccessible locations.

As an alternative to cryogenic fractionalization, a variety of small-scale techniques have been developed for producing relatively pure gases. For example, hydrogen and oxygen may be produced by the electrolysis of water under controlled conditions. Although practical for many applications, electrolysis suffers from relatively high energy requirements and a substantial danger of explosion resulting from the presence of molecular hydrogen. Methods have also been developed for extracting dissolved gases from liquids, particularly fresh sea water. Such methods generally employ gas-permeable membranes for extracting the gases. As with electrolysis, membrane gas extraction is useful, but suffers from a number of limitations. In particular, most membranes are nonselective and will pass whatever gases are dissolved in the sea water. Moreover, the pressure of the collected gas generally cannot exceed the partial pressure in the sea water, at least in the absence of suitable compression and storage equipment.

Recently, systems have been developed for extracting oxygen from fluid mixture feedstocks based on the use of organometallic carrier compounds which in a first oxidation state bind the oxygen molecules and in a second oxidation state release the oxygen molecules. The systems, as described in U.S. Pat. Nos. 4,602,987, 4,609,383, and 4,629,544 rely on circulating the carrier compounds past a first location where the oxygen is bound, typically through an oxygen-permeable membrane. The oxygen-loaded carrier compounds are circulated past a first electrode where their oxidation state is changed, causing release of the oxygen which then may be collected and stored or utilized. The unloaded carrier compounds are then circulated past the second electrode of the electrochemical cell, where they are returned to their first oxidation state. The carrier compounds are then returned to the loading station where they can again bind oxygen from the fluid mixture.

Such systems have several advantages. First, the energy requirement is low relative to other extraction techniques, particularly electrolytic decomposition of water. Second, the partial pressure of oxygen which may be obtained is limited only by the solubility of the carrier complexes in the circulating carrier fluid. Thus, oxygen pressures which are much higher than the partial pressure in the fluid mixture may be obtained without use of supplemental compression equipment.

Despite the substantial advances represented by U.S. Pat. Nos. 4,602,987, 4,609,383, and 4,629,544, it would still be desirable to provide improvements in the systems described. For example, the efficiency of oxygen extraction systems could be increased by optimizing the structures, and hence the electrochemical, thermodynamic, and kinetic properties of the carrier compounds. It would also be desirable to provide a more efficient transfer of electrons from the carrier compounds to the anodic electrode and from the cathodic electrode to carrier compounds. Further, enhanced oxygen extraction by promoting the transfer of electrons from the carrier compounds to the anodic electrode and/or from the cathodic electrode to the carrier compounds would be possible. Such increased efficiencies would increase the volume output of oxygen from a fixed sized cell or, alternatively, allow a fixed amount of oxygen to be produced by a cell having reduced electrode area and/or lower power consumption.

The use of transition metal complexes of linear, pentadentate polyalkylamines in electrochemical oxygen extraction and generation processes is described in copending applications, assigned to the same assignee as the present application: Ser. No. 018,891, filed Feb. 25, 1987; Ser. No. 018,895, filed Feb. 25, 1987; and Ser. No. 018,888, also filed Feb. 25, 1987; the disclosures of each of these copending applications are hereby incorporated herein by reference.

2. Description of the Background Art

Some types of such transition metal carrier complexes have been used in or suggested for use in devices for extraction, absorption, and generation of oxygen from fluid media. For example, Roman, U.S. Pat. Nos. 4,451,270 and 4,542,010, discloses various metal complexes in a non-electrochemical oxygen extraction system utilizing an oxygen selective, permeable membrane. The carriers include cobalt complexes of linear and macrocyclic tetradentate, linear pentadentate, and bindentate Schiff base ligands in primarily non-aqueous, Lewis base solvents; all disclosed systems appear to require the use of an axially-coordinating base. Hill, U.S. Pat. No. 4,442,297, uses phosphine complexes of Mn(II) in dehydrated solvents to purify nitrogen gas by extracting impurities including molecular oxygen. Sievers, U.S. Pat. No. 4,514,522, discloses oxygen sorbents comprising linear, tetradentate ketoamine complexes bound to porous polymers. Gagne, U.S. Pat. No. 4,475,994, uses cobalt complexes of unknown stoichiometry in a mixed solvent at high pH to transport electrochemically generated superoxide ions across a fluid membrane. Bonaventura, et al., U.S. Pat. Nos. 4,602,987; 4,609,383 and 4,629,544, disclose a variety of metalloporphyrins and macrocylic ligand complexes, in combination with axially coordinating Lewis bases, in aqueous, non-aqueous, and water-immiscible solvents and their use to electrochemically separate oxygen from fluids.

Oxygen carrier compounds, including cobalt complexes of some macrocyclic amines, and their thermodynamic properties have been extensively reviewed and tabulated. Niederhoffer, et al., Chem. Rev. 84 137–203 (1984).

Oxygenation equilibria and kinetics of macrocyclic amine complexes of cobalt ion have been studied by C-L. Wong, et al., 102 *J. Am. Chem. Soc.* 5511-18 (1980). T. Geiger and F. C. Anson, 102 *J. Am. Chem. Soc.* 7489-96 (1981) have investigated the catalysis, by Cobalt (III) complexes of macrocyclic amines, of the electromechanical reduction of molecular oxygen. The use of such complexes for the electrochemical extraction and regeneration of oxygen is not known.

SUMMARY OF THE INVENTION

Methods and apparatus for extraction of a ligand such as molecular oxygen from a first fluid environment and for release of a ligand such as molecular oxygen to a second fluid environment are disclosed, as well as ligand carrier compounds therefor comprising tetra-, penta-, and hexa- dentate macrocyclic amines and transition metal ions. The carrier compounds have the general formulae:

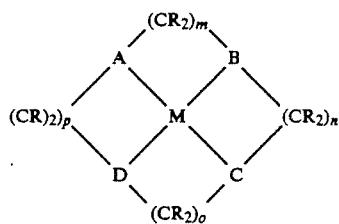

and:

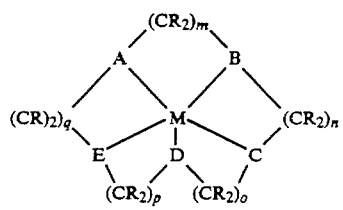

and:

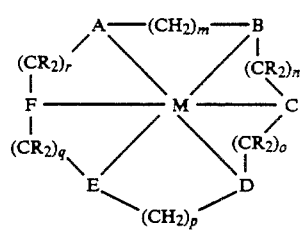

where:
A, B, C, D, E and F are each nitrogen, oxygen, sulfur, or phosphorous;
m, n, o, p, q and r are each typically 2, 3, 4, 5 or 6;
the R substituents are each generally H or short chain (linear or branched) alkyl, although $R_2$ may represent ketyl ($=O$); and
M is a suitable transition metal ion.

For use in the methods and apparatus according to the invention, the carrier compounds are contained in a suitable aqueous carrier fluid comprising the carrier compound and a supporting electrolyte, adjusted to an appropriate pH. Carrier fluids according to the present invention do not include an added Lewis base for axial coordination to the transition metal ion in the carrier compound.

Typical methods according to the invention include: contacting a first fluid environment containing a ligand with the first surface of a first ligand permeable membrane having a first and second surface wherein the membrane separates the environment from an interior space of a container; contacting a carrier fluid with the second surface of the membrane wherein the carrier fluid is confined in the container and the carrier fluid contains a carrier compound, whereby at least a portion of a ligand which diffuses through the membrane binds to the carrier compound to give bound ligand complex; transporting the carrier fluid containing the bound ligand complex to a first electrode compartment of an electrochemical cell which forms a second portion of the container; electrochemically modulating the carrier compound to an oxidation state having relatively less binding affinity for ligand, thereby releasing free ligand into the carrier fluid and producing a non-binding state carrier compound; removing ligand from the carrier fluid to give a ligand depleted carrier fluid; transporting the ligand depleted carrier fluid containing the non-binding state carrier compound to a second electrode compartment of an electrochemical cell which forms a third portion of the container; and electrochemically modifying the non-binding state carrier compound to reform the binding state carrier compound.

Typically, an apparatus used for the extraction of a ligand such as oxygen from fluids, for example, air or seawater, will comprise an oxygen loading station in which an oxygen (or ligand) binding carrier compound in its reduced valence state is transported past an oxygen permeable membrane in contact with the first fluid environment from which oxygen is being extracted. A carrier fluid containing the carrier compound is transported through an apparatus through a conducting system which seals the carrier fluid from both the first fluid environment (occasionally referred to herein as an external fluid environment) and a second fluid environment (sometimes referred to herein a the internal environment) into which oxygen is being released. The reduced state oxygen carrier is oxidized at the anode of an electrochemical cell, and the carrier fluid containing free dissolved or gaseous oxygen is transported to a separate location, generally, an "unloader," where the oxygen passes into the interior environment, in some embodiments, through an oxygen permeable membrane. The carrier fluid containing the oxidized-state carrier compound is then circulated back through a cathode compartment of an electrochemical cell where the reduced state oxygen carrier is reformed by electrochemical reduction. The carrier fluid containing the reduced state oxygen carrier is then transported back to the oxygen loading station, after which the entire operation can be repeated.

The type of electrode is not critical, generally being a chemically inert carbon or metallic electrode, often being porous to provide a large surface area and good contact with the circulating carrier fluid. However, the kinetic, thermodynamic, and electrochemical behavior of different carrier complexes may vary with different electrodes; accordingly, in certain embodiments of the invention, one or another electrode material and/or type will be preferred.

Other methods and apparatus according to the invention utilize diffusive transport of oxygen or other ligands as ligand-carrier complexes between electrodes of an electrochemical cell either in conjunction with ligand permeable membranes or using ligand permeable electrodes.

Another aspect of the invention relies on the use of an electrocatalyst to promote electron transfer between the carrier compounds and either or both of the electrodes of the electrochemical cell. The electrocatalyst is a substance capable of rapid electron transfer which has an electrical potential less than that of the carrier compounds under the operating conditions of the cell. That is, the energy required to transfer electrons to and from the electrocatalyst will be less than that required to transfer electrons to and from the carrier compounds directly. The electrocatalyst may be immobilized on either or both of the electrodes or, more usually, will be present in the carrier fluid so that it circulates together with the carrier compounds.

As just described, the voltage required to operate the electrochemical cell is decreased as a result of substituting the oxidation/reduction of an electrochemical catalyst having a lesser potential than that of the carrier compound. For most of the electrocatalysts described below, the difference between the standard potential of the electrocatalysts and that of the oxygenated carrier complex is in the range from about −1.0 to −0.0 volts, more usually from about −0.5 to −0.2 volts.

References herein to tetra-, penta- and hexadentate ligands or coordination refer to the number of atoms that are available in a ligand for coordination to a metal ion and do not necessarily imply that all such atoms are coordinated to the metal ion at all times or under all conditions.

Although reference will be made to "oxygen carriers" and "oxygen binding compounds," many of the carrier compounds according to the invention reversibly bind other small molecules, or "ligands," such as carbon monoxide, carbon dioxide, nitric oxide, cyanide, isocyanide, hydroxide, and the like. It will be understood that the invention is intended to comprehend extraction (from an appropriate fluid medium), transport, and regeneration or release of such ligands as well as oxygen, where the carrier compounds of the invention reversibly bind such ligands and have differential affinities for such ligands in the oxidized and reduced states of the carrier compounds.

BRIEF DESCRIPTION OF THE DRAWINGS

A more complete appreciation of the invention and many of the attendant advantages thereof will be better understood by reference to the following detailed description of the specific embodiments hereof when considered in connection with the accompanying drawings, wherein:

FIG. 1A is a plot of cyclic voltammetry traces for the deoxygenated cobalt carrier compound of 1,4,8,12-Tetraazacyclopentadecane in aqueous 0.5 M KCl solution, pH 8.3, using an initial voltage of 0.0 V vs. an SCE reference electrode, an initially positive sweep rate of 50 mV/s, and the noted working electrodes.

FIG. 1B is a plot of cyclic voltammetry traces for the oxygenated cobalt carrier compound of 1,4,8,12-Tetraazacyclopentadecane in 0.5 M KCl solution, pH 6.5, using an initial voltage of 0.0 V vs. an SCE reference electrode, an initially positive sweep rate of 50 mV/s, and the noted working electrodes.

FIG. 1C is a plot of cyclic voltammetry traces for the cobalt carrier compound of 1,4,8,11-Tetraazacyclotetradecane in the presence (b) and absence (a) of oxygen using an initial voltage of 0.0 V vs. an SCE (Standard Calomel Electrode) reference electrode, an initially positive sweep rate of 50 mV/s, and a graphite working electrode.

FIG. 2A is a plot of cyclic voltammagrams of Dimethylaminomethylferrocene (1 mM) in aqueous 0.5 M KCl solution, pH 6.4, at a gold working electrode at the sweep rates (in V/s) indicated: (a) in the absence of carrier compound; and (b) in the presence of oxygenated Co(II)(1,4,8,12-Tetraazacyclopentadecane) (10 mM).

FIG. 2B is a plot of cyclic voltammagrams of Dimethylaminomethylferrocene (1 mM) in aqueous 0.5 M KCl solution, pH 7.0, at a gold working electrode at the sweep rates (in V/s) indicated: (a) in the absence of carrier compound; and (b) in the presence of oxygenated Co(II)(1,4,8,11-Tetraazacyclotetradecane) (20 mM).

FIG. 3 is a schematic diagram illustrating an apparatus for practice of the methods of the invention.

FIG. 4 is a schematic diagram illustrating an Electrochemical Oxygen Cell (EOC) used for preliminary evaluation of the properties of individual carrier compounds for use practicing the methods of the invention.

FIG. 5 is a schematic diagram of a specific embodiment of an apparatus for the practice of the methods of the invention, showing manufacturing parameters for this apparatus.

FIG. 6 is a schematic diagram of a second specific embodiment of an apparatus for the practice of the methods of the invention.

FIG. 7 is a schematic illustration of a bipolar cell useful for extracting oxygen from an oxygenated carrier compound according to the present invention.

DETAILED DESCRIPTION OF THE SPECIFIC EMBODIMENTS

The chelating ligands which may be used to form the transition metal carrier compounds of the present invention and of potential use in electrochemical ligand extraction, transport, and generation processes according to the present invention are macrocyclic and tetradentate, pentadentate, or hexadentate. The macrocyclic amine ligands of a type useful in the present invention will include those of the general formulas:

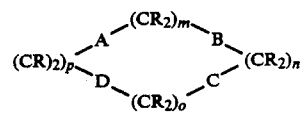

and:

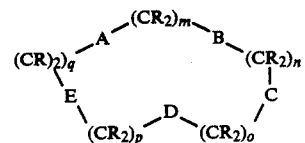

and:

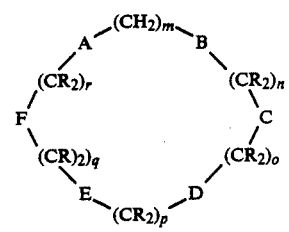

where:

A, B, C, D, E, and F are each nitrogen, oxygen, sulfur, or phosphorous;

m, n, o, p, q, and r are each typically 2, 3, 4, 5 or 6, more usually 2 or 3; and the R substituents are each generally H or short chain (linear or branched) alkyl, although $R_2$ may represent ketyl (=O); and At least one but usually three, and more usually four, of the atoms available for coordination (A, B, C, D, and/or E) to the selected transition metal ion (generally referred to herein as "ligating atoms") will be nitrogen. The remaining ligating atom(s) will usually be nitrogen, oxygen, sulfur or phosphorous. Ligating nitrogens may be of the secondary or tertiary aliphatic, usually >NH, or aromatic type, such as pyridyl, imidazolyl, or pyrrolyl; one or more such types of nitrogen may generally be present in the same macrocyclic amine ligand. Ligating oxygen, when present in a particular ligand, will usually be of the ether type, while ligating sulfur will be a thioether.

Usually, the R groups will all be hydrogen, but alkyl substituted chains connecting the ligating atoms may be preferred in some instances; the steric effects of such side chains may desirably alter the function and/or performance of carrier compounds in processes according to the invention.

Specific examples of macrocyclic amine ligands in which each of the ligating atoms is nitrogen include:

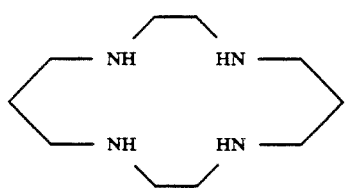

that is, A=B=C=D=NH, m=o=2, n=p=3, and R=H: 1,4,8,11-Tetraazacyclotetradecane, sometimes abbreviated in the literature as "cyclam;"

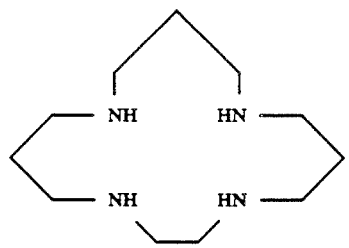

that is, A=B=C=D=NH, o=2, m=n=p=3, and R=H; 1,4,8,12-Tetraazacyclopentadecane;

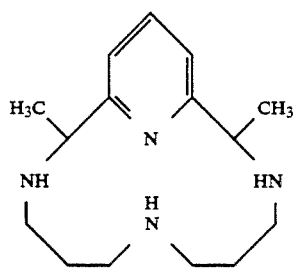

that is, A=pyridyl, B=C=D=NH, m=o=2, n=p=3, R(C2)=R(C12)=CH$_3$, and all other R=H: 2,12-dimethyl-3,7,11,17-tetraaza bicylco[11.3.1]heptadeca-1(17),13,15-triene;

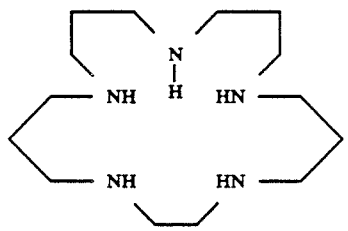

that is, A=B=C=D=E=NH, m=n=p=q=3, o=2, R=H: 1,4,8,12,16-Pentaazacyclononadecane; and

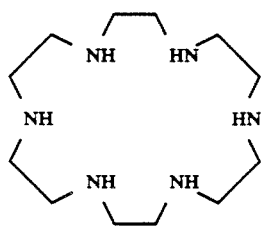

that is, A=B=C=D=F=NH, m=n=o=p=q=r=2, R=HL 1,4,7,10,13,16-Hexaazacyclooctadecane.

EXAMPLE I

Preparation of 1,4,8,11-Tetraazacyclotetradecane

Approximately 0.5 mole (118 gm) NiCl$_2$.6H$_2$O is dissolved in about 100 ml of water and treated with 0.5 mole (87 gm) N,N'-bis-amino propyl ethylene diamine (1,4,8,11 -tetraazaundecane). The resulting orange to brown solution to treated with a slight molar excess of glyoxal (≧29 gm.) as a 30–40% aqueous solution and allowed to stand for about 12 hours. After cooling to about 5° C., the resulting mixture is slowly added to 1 mole (37.8 gm) of sodium borohydride, in a minimum of 1:1 ethanol-water, avoiding frothing.

The solution is then heated to about 95° C. and filtered hot; after slight cooling, the filtrate is neutralized with perchloric acid. Further cooling yields crystalline Ni (1,4,8,11-tetraazacyclotetradecane)Cl$_2$. To prepare the free ligand, a greater than four-fold molar excess of sodium cyanide as an aqueous solution is added to an aqueous solution of the nickel complex. On warming, an orange color due to Ni(CN)$_4^{2-}$ appears. The pH of the solution is then adjusted to >12 with aqueous NaOH, after which the solution is extracted with 6×50 ml aliquots of chloroform. On evaporation of the chloroform, an off white solid is obtained, which is then recrystallized from hot tetrahydrofuran by the addition of pentane to yield the desired product.

EXAMPLE II

Preparation of 2,12-dimethyl-3,7,11,17-tetraazabicyclo[11.3.1]heptadeca-1(17),13,15-triene Solutions of 2,6-diacetylpyridine (13 gm, 0.08 mole) in 160 ml of ethanol and NiCl$_2$.6H$_2$O (19 gm, 0.08 mole) in 240 ml of water are mixed and heated to ca. 65° C.;

3,3′-diaminodipropylamine (10.5 gm, 0.08 mole) is added dropwise. The resulting slightly cloudy solution is clarified by the addition of 5 ml acetic acid; after heating at 65° C. for about 5 hours, the ethanol is removed by evaporation and the solution is filtered. Addition of 50 ml concentrated aqueous sodium perchlorate precipitates the crude unsaturated nickel complex, which is removed by filtration, washed with ethanol, and recrystallized from warm (65° C.) water by the addition of 30 ml of 70% perchloric acid and slow cooling. The unsaturated nickel complex of 2,12-dimethyl-3,7,11,17-tetraazabicylo[11.3.1]heptadeca-1(17),2,11,13,15-pentaene is hydrogenated by adding PtO catalyst (0.01 gm) to a solution of the nickel complex (5.16 gm. 0.01 mole) in 300 ml water, which is then shaken in a Parr hydrogenation autoclave (initially at an H$_2$ pressure of 50 atm.) for about 24 hours. After filtration to remove the catalyst, the crude nickel complex of the desired ligand is obtained by evaporation of the solvent. The free ligand is produced by adding NaCN (1.5 gm. 0.03 mole) to a warm (80° C.) solution of 2.6 gm (0.005 mole) of the nickel complex in 100 ml of water, stirring for ca. 20 min. at 80° C., and making the solution strongly basic. After cooling, the solution is extracted with twenty 20 ml portions of ether which is evaporated to yield the desired ligand.

The carrier compounds may be coordination complexes of the above macrocyclic amine ligands with any of a variety of transition metals including titanium, manganese, chromium, iron, cobalt, nickel, copper, ruthenium, rhodium, palladium, osmium, iridium, and platinum; usually, the transition metal will be manganese, iron, or cobalt, but the invention is not so limited. Other transition metals that form complexes that reversibly bind molecular oxygen may also be used; complexes of such metals are contemplated to be within the scope of the present invention. The primary requisites of the transition metal are that it form complexes, have a first valence state in which the transition metal complex reversibly binds molecular oxygen or another ligand of interest, and have a second valence state in which the transition metal complex has a substantially lower affinity toward molecular oxygen or other ligand. Preferably, the metal is chosen to be, in its second valence state, substantially unreactive with molecular oxygen or other ligand of interest. In addition, the valence state of the transition metal(s) used will be electrochemically modulable. In known transition metal complexes which will be suitable for use, the valence state in which oxygen is reversibly bound will be lower (more reduced), e.g., Mn(II), Fe(II), Co(II) or Cu(I); this lower valence state will be generally referred to herein as the "binding state." The non-binding valence state (generally referred to herein as the "non-binding state") will generally be higher and achieved via a one electron oxidation of the lower valence state, e.g., Mn(III), Fe(III), Co(III), or Cu(II).

The carrier compounds according to the present invention comprise, generally, ions of one of the above transition metals reacted with a macrocyclic amine ligand. The carrier compounds may be prepared and isolated as will be outlined below. Alternatively, since many of the macrocyclic amines according to the present invention have a very high affinity for metal ions such as cobaltous ion, suitable carrier compounds may be prepared in situ during the preparation of carrier solutions for the extraction, transport, and regeneration of small ligands, e.g., molecular oxygen. Preparation of carrier compounds in situ is accomplished in such instances by the addition of equimolar amounts of the metal ion, e.g., 1 millimole/liter Co$^{2+}$, and macrocyclic amine, e.g., 1 mM/L, to a particular carrier fluid.

Carrier compounds useful in the present invention will thus have the general formula M(L)$^{n+}$, where M is a transition metal ion and L is a macrocyclic amine ligand. The charge on the carrier compound will depend on the valence state of the metal ion, the extent of ionization of the macrocycle, the pH of the carrier solution, etc. Sufficient counterions will accompany carrier compounds (whether as solids or in solution) to counterbalance this charge. The counterions will usually be anions and will be both chemically and electrochemically unreactive under the conditions to be employed for extraction, transport, or regeneration of molecular oxygen. Counteranions will typically be small, unreactive anions such as: halide ions, e.g., fluoride, chloride, bromide, or iodide; oxyanions, e.g., nitrate, sulfate, or phosphate; or organic ions, e.g., acetate or citrate. For convenience, the carrier compounds may be designated herein M(L); it will be understood that this designation will include both charged and uncharged carrier compounds and that charged carrier compounds will be understood to be accompanied by suitable counterions. Carrier compounds according to the present invention will thus generally be metallic complexes having the general formulae:

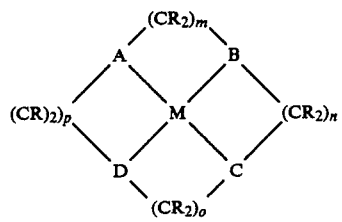

and:

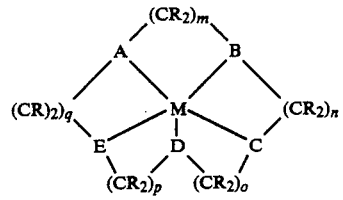

and:

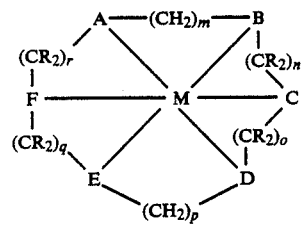

where:
A, B, C, D, E, and F are each nitrogen, oxygen, sulfur, or phosphorous;
m, n, o, p, q and r are each typically 2, 3, 4, 5 or 6;
the R substituents are each generally H or short chain (linear or branched) alkyl, although R$_2$ may represent ketyl (=O); and
M is a suitable transition metal ion.

EXAMPLE III

Preparation of Co(II)(1,5,9,13,17-Pentaazacyclononadecane)Cl₂

A solution of 15.6 gm (0.043 mole) of Ni(ClO₄)₂.6-H₂O, 8 gm (0.043 mole) of tetrapropylenepentamine pentamine (1,5,9,13,17-pentaazaheptadecane), and 8 ml of glyoxal in 150–200 ml of water is heated to about 60° C. for two hours. Raney nickel catalyst is added and the solution is shaken at 60°–70° C. under 50 psi of H₂ for 12–14 hours. After removal of the catalyst, the solution is treated with 10 gm of sodium cyanide and warmed until the orange color of Ni(CN)₄²⁻ was obtained. The pH of the solution is adjusted to >12 with NaOH; six 50-ml extractions are made with CHCl₃. Evaporation of the chloroform yields an off-white solid that is recrystalized from hot tetrahydrofuran by addition of pentane. The cyclic pentadentate ligand obtained can be converted to the cobalt salt by dissolution in a minimum of water and addition of an equimolar amount of cobalt chloride, also in a minimum of water.

Alternatively, this compound can be prepared by cyclization of the linear pentadentate amine about cobalt ion. By this method, a solution of 17 gm (0.046 mole) of Co(ClO₄)₂.6H₂O in 125 ml of oxygen-free water is added under nitrogen to 8.1 gm (0.46 mole) of tetrapropylenepentamine. Glyoxal (7.7 ml as a 40% solution in water) is added with good stirring and the solution is allowed to stand overnight, after which a deep wine-red solution is present. After cooling of the solution to about 5° C., 3.4 gm (ca.0.1 mole) of NaBH₄ is slowly added in small portions. The solution is heated to near boiling and then, after cooling somewhat, acidified with concentrated HCl and filtered in the air. Upon cooling, green crystals form. These are collected, washed with ethanol in ether, and air-dried to yield the desired cobalt complex.

Each of the above disclosed carrier compounds will be useful in the electrochemical extraction, transport, and generation of oxygen and other small ligands according to the methods of the present invention. However, the selection of particular carrier compounds according to the invention for optimization of the practice of the methodology and processes depends on a variety of factors. Further, the carrier compound preferred for a particular apparatus and process will depend on the characteristics and operating environment of the apparatus and associated power supplies and sources, fluid media used to supply ligand, the intended use of the extracted ligand, and other considerations. Although the following will make particular reference to oxygen binding to cobalt complexes of particular macrocyclic amines, it is understood that the invention is not so limited.

The initial pH for use in the experiments to be described below (the "Working pH") is defined as one pH unit above that at which the proportion of carrier compound-oxygen complex is about 50% or more of the maximum formed under ca. 0.2 atm oxygen, as determined by UV-Visible spectroscopic examination or potentiometric titration as described in our co-pending application Ser. No. 018,891, filed Feb. 25, 1987. At this working pH, the formation of oxygen complex of cobalt carrier compounds, when the cobalt carrier compound is exposed to molecular oxygen, is heavily favored; in addition, the pH is generally low enough at the working pH to avoid decomposition of the particular carrier compound or spontaneous oxidation of the cobalt ion.

This working pH is an initial estimate of a pH for the carrier fluids and practice of the methods of the invention. Experimentation involving varying the pH of the carrier fluids may indicate a more efficacious pH for actual use in the methods. Usually, the pH will be chosen such that at least half of the maximal concentration of carrier compound oxygen complex is formed, more usually, the pH is selected so that at least 75% of the maximal concentration is formed, and preferably the pH is selected so that 90% or more of the maximal proportion of oxygen complex is present, all under a pressure or partial pressure of ca. 0.2 atm oxygen.

The macrocyclic amine carrier compounds according to the present invention may form both monomeric and dimeric complexes with molecular oxygen, although typically the dimeric complex is more readily and frequently observed. Using cobalt carrier compounds as an example, the following equilibria may generally be observed in aqueous solution, depending on such factors as the pH of the carrier fluid, the identities and relative concentrations of the various species, the temperature, and the solvent.

$$L + Co^{2+} = Co(L)^{2+} \tag{1}$$

$$Co(L)^{2+} + O_2 = Co(L)(O_2)^{2+} \tag{2}$$

$$Co(L)(O_2)^{2+} + Co(L)^{2+} = [Co(L)]_2O_2^{4+} \tag{3}$$

$$2Co(L)^{2+} + O_2 = [Co(L)]_2O_2^{4+} \tag{4}$$

Reaction (1) can be characterized by the equilibrium constant $K_{ML}$, given by:

$$K_{ML} = [Co(L)^{2+}]/[L][Co^{2+}]. \tag{5}$$

For the carrier compounds according to the present invention, usually only the dimeric oxygen complex is observed in solution, so that the equilibrium between oxygen and carrier compound is effectively characterized by $K_{app.O_2}$ for the combination of reactions (2), (3), and (4), given by:

$$K_{app.O_2} = [[Co(L)]_2O_2^{4+}]/[Co(L)^{2+}]^2[O_2]. \tag{6}$$

From the $K_{O_2}$ values, the change in the free energy for the oxygenation of the cobalt carrier compounds and thus the minimum power requirements for the electrochemical release of oxygen can be calculated. For the overall equilibrium given by equation (4) above, the standard free energy in calories/mole is given by $$\Delta G° = -RT \ln K_{O_2} = -nFE°_{O_2} \tag{7}$$

where:

T is the temperature in Kelvins; R is a constant of 1.987 cal/mole-K; F=96.487 C/mole; $K_{O_2}$ is given by equation (8); and $E°_{O_2}$ is the standard potential for the reaction of equation (4) For a two electron process (n=2), RT/nF=0.01285 V. For nonstandard states (i.e. where the chemical activities of the species in solution are not equal to one):

$$\Delta G = \Delta G° + RT \ln Q \tag{8}$$

and $$E_{O_2} = E°_{O_2} + RT/nF \ln Q = 0.01285 \ln(K_{O_2}/Q) \tag{9}$$

where the concentrations actually present in solution are used to calculate Q from $$Q = [(Co(L))_2O_2]/[Co(L)]^2[O_2]. \quad (10)$$

Assuming the total carrier compound concentration is initially 0.1 mole/liter, that half of the cobalt ion is oxidized electrochemically to release oxygen, and that the resulting concentration of oxygen (in solution) is 1.5 mM, for the carrier compound equilibrium of equation (4).

$$Q = (0.25x)/(A-0.5x)^2 [O_2] \quad (11)$$

where A is the initial carrier compound concentration and x is A times the percentage of carrier compound which is present as the oxygen complex, the minimum voltage, E, for the process can be determined. If the total oxygen to be released is 1 L/min, the total current, I, required is 71.8 n amperes, where n is the number of electrons per oxygen released, and the minimum power, in Watts, required is given by P=71.8 n E. This is the minimum power required, and neglects such factors as parasitic power losses due to the resistance of the carrier fluid. Calculations of the voltage and power required for various dimeric cobalt carrier compounds indicate required cell voltages between about 100 and about 400 mV and power requirements of between about 15 W/L and about 50 W/L of $O_2$ released per minute.

It is possible to carry out the redox process on the oxygen carrier directly without the intervention of any modifier, promoter, linker, mediator, or other electrocatalyst. However, such materials may be included if desired, and, according to another aspect of the invention, can significantly increase the efficiency of oxygen extraction. A mediator is a small molecule also present in a circulating carrier fluid which serves to transport charge from the electrode surface to the oxygen carrier. A modifier or promoter is a molecule attached to the electrode surface which facilitates electron transfer without itself undergoing a redox reaction. A linker is a molecule which binds the carrier to the electrode surface where the redox process can take place.

The substance used as the electrocatalyst may be any atomic species, compound, or aggregate which fulfills certain physical requirements. The substance must be able to rapidly transfer electrons between the electrodes and the carrier compound in order to allow indirect oxidation/reduction of the carrier compound. Additionally, the electrical potential required to transfer electrons between the electrodes and the electrocatalyst must be less than that required for electron transfer between the electrodes and the carrier compounds under the operating conditions of the cell. Usually, this corresponds to a lower standard potential for the electrocatalyst than for the oxygenated carrier compound. The standard half-cell reaction for oxidation of the electrocatalyst (EC) can be written as follows:

$$EC = EC^+ + e^-, \quad E^\circ_{ec} \quad (12)$$

where $E^\circ_{ec}$ is the oxidation potential of the electrocatalyst. Although the exact mechanism will vary with particular carrier compounds and electrocatalysts, in the presence of a suitable catalyst, the overall oxidation reaction will proceed as follows:

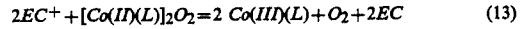

$$2EC^+ + [Co(II)(L)]_2O_2 = 2 Co(III)(L) + O_2 + 2EC \quad (13)$$

Thus, $E^\circ_{ec}$ will be less than $E^\circ_{CoO_2Co}$ the oxidation potential for the reaction:

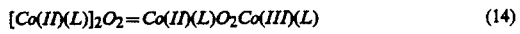

$$[Co(II)(L)]_2O_2 = Co(II)(L)O_2Co(III)(L) \quad (14)$$

providing a decreased potential for driving the oxidation of the carrier compound and release of oxygen.

The electrical potential of the electrocatalyst normally is not be too far below that of the oxygenated carrier compounds, or an unfavorable thermodynamic equilibrium may result. Usually, the electrocatalyst will have a potential below that of the carrier compound by about 0.0 to 1.0 volts, usually by about 0.2 to 0.5 volts.

Suitable electrocatalysts are selected based on their oxidation/reduction potentials relative to the carrier compounds. Such selection could be made by measuring the potentials for both the electrocatalyst and the carrier compound by conventional techniques, typically using a calomel or other standard electrode. Conveniently, selection may be made by simply testing the effectiveness of a candidate electrocatalyst in lowering the potential required to release oxygen in a coulometric experiment as follows. Oxygenated carrier compound is placed in a cell having a working electrode and an auxilliary electrode. The electrodes are separated by an ion permeable membrane, and the oxygenated carrier compound is in contact only with the working electrode. A suitable electrolyte is placed in contact with the auxilliary electrode. The voltage required to release oxygen from the oxygenated carrier compound can then be determined by simply stepping the voltage until oxygen release is detected, typically using a conventional oxygen probe. The experiment may then be repeated with the addition of the electrocatalyst, either in solution or immobilized on the electrode, in order to determine the decrease in potential required for the release of oxygen. If the decrease is in the suitable range from about 0.0 to 1.0 volts, usually from about 0.2 to 0.5 volts, the electrocatalyst will be effective in reducing the energy consumption in an electrochemical cell as described above.

A variety of compounds are generally suitable as electrocatalysts, although testing of the individual compounds with particular carrier compounds is still required. The classes of electrocatalysts which are suitable for use in the present invention include anions, such as iodide, bromide, and nitrate; cations, such as ruthenium pentamine pyridine complex and 2,2'-bipyridyl cerium; phenolic compounds, such as catechols, hydroquinones, dopamines, indophenols, and phenolic ether compounds; sulfonic ether compounds (sulfur analogs of the phenolic ether compounds just listed); organometallic compounds, such as ferrocenes, particularly ferrocenecarboxylic acid, cobaltocenes, nickelocenes, and metal carbonyls; metal porphyrins which do not reversibly bind oxygen under the conditions used such as iron tetraphenylporphyrin and metal corrin compounds, particularly vitamin B-12; metal macrocyclic compounds, such as cobalt phthalocyanines, iron phtyalocyanines, metal cyclams, particularly nickel cyclam, and metal salen complexes; amines, such as p-phenylenediamine, N,N,N',N'-tetramethylphenylenediamine, and tris(p-bromophenyl)amine; thiazines, such as methylene blue and new methylene blue; delocalized aromatic molecules, such as Koelsch's radical; cytochrome molecules, hydroxylamines, metal phosphine complexes, such as nickel triphenylphosphine; and the like. Preferred electrocatalysts include substituted ferrocenes, for example 1,1'-ferrocenedicarboxylic acid or N,N-dimethylaminomethylferrocene, iodide ions, phenylenediamines, for example, N,N,N',N'-tetramethyldiaminobenzene, and substituted quinones.

Once the electrocatalyst has been selected, it must be introduced to the oxygen extraction system. Usually, the electrocatalyst will be dissolved or mixed with the circulating carrier fluid, although it will sometimes be desirable to immobilize the electrocatalyst on the electrodes or on a support other than the electrodes. By including the electrocatalyst in the carrier fluid, the oxidation/reduction reactions may take place in the carrier fluid away from the electrode surfaces. This geometric effect increases the frequency of encounters between the carrier compounds and the electrocatalysts, and thus promotes the net electron transfer between the electrodes and the carrier compound. Such promotion is in addition to the primary catalytic effect, i.e., lowering of the energy required to transfer electrons between the electrodes and carrier compound, discussed above. In some cases, it may be desirable to covalently link the electrocatalyst to the carrier compound.

Depending on its solubility, the electrocatalyst may be present in the carrier fluid at a concentration from about 0.01 mM to about 1 M, more usually from about 0.1 mM to 0.1 M, more usually from about 0.1 mM to 100 mM. Usually, it will be desirable to maintain an electrocatalyst concentration having an equivalent ratio to the carrier compound concentration of at least 1:1000 (e.g., electrocatalyst:eq. carrier compound), usually at least 1:500, more usually at least 1:200, and frequently higher, with the upper limit being the solubility or the concentration where the electrocatalyst interferes with the ability of the carrier compound to take up oxygen. For the preferred electrocatalysts, a concentration of approximately 0.5 to 30 mM, more usually 1–10 mM, has been found effective.

As demonstrated more fully in the examples below, using the electrocatalysts of the present invention substantially reduces the operating voltage required to effect the oxidation/reduction of the carrier compounds with the accompanying release of oxygen. Typically, operating voltages will be decreased by about 0.1 to 0.5 volts, usually about 0.2 to 0.4 volts, when the electrocatalysts of the present invention are employed. This decrease, in turn, provides for a substantial reduction in energy consumption as the current load remains constant for a given volume of oxygen.

EXAMPLE IV

Electrochemical Experiments

Characterization by cyclic voltammetry and controlled potential electrolysis is performed to identify those cobalt carrier compounds for which electrical operating parameters, such as the voltage and current requirements of apparatus for practicing the methods of the present invention, would be most convenient with minimum actual power consumption.

1. Procedures

Cyclic voltammetry experiments were performed under nitrogen or air for the unoxygenated or oxygenated carrier compounds, respectively, in a cell having a platinum wire auxiliary electrode, a silver-silver chloride reference electrode, and a suitable working electrode. The potential between the auxiliary and working electrodes was varied with a Princeton Applied Research (Princeton, N.J.) Scanning Potentiostat at 50 mV/s from a suitable $E_{initial}$, with a suitable initial scan direction (Scan Dir.), depending on the electrochemical potentials of interest. All solutions contained 1 mM $CoCl_2$, 1 mM or 1.5 mM of macrocyclic amine ligand, and a supporting electrolyte, and were buffered or adjusted to a suitable pH, usually about the initial working pH.

Cyclic voltammetry enables the estimation of anode $(E_{PA})$ and cathode $(E_{PC})$ half cell potentials, the cell potential, $\Delta E = (E_{PA} - E_{PC})$, and an approximate formal reaction potential $E^* = (E_{PA} - E_{PC})/2$. In addition, estimates of the rate of electron transfer to a particular electrode and the electrochemical reversibility of the reaction can be obtained. However, cyclic voltammetry experiments do not show whether or to what extent molecular oxygen is released.

Controlled Potential Electrolysis techniques allow the determination of the relative energetics and rates of oxygen release. For such experiments, solutions similar to those outlined above for cyclic voltammetry are placed in a three-electrode electrolysis cell equipped with a Clarke-type oxygen probe. The carrier compound is electrochemically reduced, oxygenated, and then reoxidized by the application of a series of oxidizing potentials. Each such oxidizing potential is held constant with respect to a silver-silver chloride reference electrode. The resulting current is integrated over time to yield the amount of carrier compound oxidized. By employing the same electrode geometry, solution volume, and stirring rate, information about the relative rate and amount of oxygen release (the "$O_2$ rate") can be determined, at a particular applied cell voltage, $E_{app}$, from the response of the oxygen probe.

The expected amount of oxygen evolved is given by one-half the total integrated charge through the cell divided by F=96.484 C/mole, since, theoretically, 2 electrons are required to oxidize two cobalt ions and release one oxygen molecule. The ratio of this figure to the actual amount of oxygen produced is "% $O_2$ max.", at the minimum voltage, $V_{min}$, required to produce oxygen. In addition, the "voltage window," the difference between the anodic oxygen evolution and cathodic reduction potentials, is measured.

2. Results

Cyclic voltammetry traces for cobalt complexes of two macrocyclic amine ligands, using working electrodes of various compositions, are shown in FIGS. 1A–1C. FIGS. 1A and 1B show such plots for cobalt complexes of 1,4,8,12-Tetraazacyclopentadecane in deoxygenated and oxygenated solutions, respectively.

The cyclic voltammetry trace of FIG. 1A shows the expected behavior of de-oxygenated cobalt complex: the wave at about 0.4 V corresponds to the oxidation of the Co(II) complex to Co(III), while the reduction wave at about 0 V represents the reverse reaction. Essentially the same behavior is observed between pH 5 and pH 8. FIG. 1B shows an oxidation wave at a similar potential due to the two electron oxidation of the dimeric oxygen complex, resulting in the release of oxygen. In addition, this figure shows two reduction waves. The first, at about 0 V, is absent unless the voltage is first swept through the 0.4 V oxidation, and thus is due to the reduction of the unoxygenated Co(III) complex.

The wave observed at about −0.4 V corresponds to the reduction of the oxygenated complex.

The electrochemical behavior of this carrier compound is seen most clearly in the results of the experiments using the gold working electrode; however, it can be seen that the results are qualitatively similar for carbon and graphite, which more closely duplicate the conditions to be encountered in the oxygen extraction apparatus to be described below.

FIG. 1C depicts the results of cyclic voltammetry of the carrier compound of cobalt ion with cyclam; these results are generally similar to those with cobalt 1,4,8,11-Tetraazacyclotetradecane complexes on working electrodes of the same material, graphite.

FIGS. 2A and 2B depict cyclic voltammetry traces of the electrochemical behavior of the electrocatalyst N,N-dimethylaminomethylferrocene in (a) the absence and (b) the presence of each of two macrocyclic amine cobalt carrier compounds. FIG. 2A shows the cyclic voltammetric behavior of 1 mM dimethylaminomethylferrocene in aqueous 0.5 M KCl solution, pH 6.4, in the absence and presence of 10 mM Co(1,4,8,12-Tetraazacyclopentadecane) and oxygen. FIG. 2B shows the cyclic voltammetric behavior of 1 mM dimethylaminomethylferrocene in aqueous 0.5 M KCl solution, pH 7.0, in the absence and presence of 20 mM Co(1,4,8,11-Tetraazacyclotetradecane) and oxygen. In these experiments, cyclic voltammetry has been performed several times with varying sweep rates, indicated adjacent to each plot, between 0.02 (20 mV/s) and 0.2 (200 mV/s). In each instance, while the electrochemical behavior of the electrocatalyst is generally unchanged (oxidation and reduction occur at the same potential), the increased magnitudes of the observed currents upon the addition of carrier compound indicate the existence of interactions between the electrocatalyst and the carrier compound. This in turn signifies that the N,N-dimethylaminomethylferrocene catalyzes the oxidation and reduction of the carrier compounds.

The results of controlled potential electrolysis experiments with these carrier compounds are summarized in Table I.

FIG. 3 shows in schematic form the operation of an idealized apparatus for use in accordance with the processes of the present invention in combination with an oxygen loading device of unspecified character. Oxygen is presumed to be the ligand in this illustration. The essential characteristics of the apparatus of the invention include a container 1 which communicates with an external environment 2 from which oxygen is to be extracted through a gas permeable membrane 3 and with an internal environment 2' into which oxygen is to be transported by means of a second gas permeable membrane 3.

TABLE I

Controlled Potential Electrolysis of Oxygen Carriers in the Presence and Absence of Electrocatalysts

| Carrier Compound | Electrocatalyst | pH | E/Volts | Q/coulombs | $O_2/\mu L/min$ |
|---|---|---|---|---|---|
| Cobalt - 1,4,8,12-Tetraazacyclopentadecane (4 mM) | | 7 | 0.25 | — | Negligible |
| | | | 0.4 | 1.5 | 1.4 |
| Cobalt - 1,4,8,12-Tetraazacyclopentadecane (4 mM) | N,N-dimethylaminomethylferrocene (1 mM) | 7 | 0.35 | 1.0 | 12 |
| Colbalt - 1,4,8,12-Tetraazacyclopentadecane (4 mM) | N,N,N',N'-tetramethyldiaminobenzene (1 mM) | 7 | 0.35 | 1.0 | 13 |
| Cobalt - 1,4,8,11-Tetraazacyclotetradecane (4 mM) | | 7 | 0.6 | 0.5 | Very Little Observed |
| Cobalt - 1,4,8,11-Tetraazacyclotetradecane (4 mM) | N,N-demethylaminomethylferrocene (1 mM) | 7 | 0.5 | 0.5 | 1.1 |

The remaining portion of the container wall in the embodiment shown is impermeable to gas, but in other embodiments is not so limited. Within the confines of container 1 is a fluid 5 which contains oxygen binding carrier compound. For purposes of illustration, the binding state is shown as a reduced oxidation state. In an oxygen loading compartment 4, oxygen becomes bound to oxygen carrier compound 6a (the reduced form of the oxygen carrier compound) to form a bound-oxygen complex 7. Complex 7 is transported along with fluid 5 to a compartment 4 where oxygen is unloaded (dissociated) from the oxygen carrier compound to which it is bound by oxidation of the reduced state oxygen carrier compound 6a to the oxidized state oxygen carrier compound 6b at anode 8 to produce free oxygen and free oxidized oxygen carriers 6b. The oxygen is separated from the oxygen carrier compound, in the embodiment shown, by diffusion through gas permeable membrane 3'. The fluid 5 containing the free oxidized oxygen carrier compound 6b is then circulated past cathode 10 where oxidized state oxygen carrier 6b is reduced to reduced state oxygen carrier compound 6a. Carrier fluid 5 containing reduced carrier compound 6a is then circulated back to compartment 4 where the process is repeated.

One apparatus for bench scale or laboratory scale evaluation of particular carrier compounds for use in practicing the methods according to the invention is illustrated schematically in FIG. 4. This electrochemical oxygen cell (EOC), designated 20, includes generally an oxygen loader 22, an electrochemical cell 24 having an anode compartment 26 and a cathode compartment 28 separated by an ion permeable membrane 30 and an unloader 32. Carrier fluid is circulated through loader 22, anode compartment 26, unloader 32, cathode compartment 28 and back to loader 22 using the pump 34 with appropriate plastic or glass conduit.

The carrier fluids suitable for use in, for example, electrochemical oxygen cell 20 comprise a carrier compound in a concentration between or about 1 mM and 500 mM, usually between about 10 and 300 mM, and most usually between about 50 and about 200 mM. Carrier fluids comprising carrier compounds according to the present invention are preferably aqueous and include in addition an electrolyte, e.g., sodium chloride, potassium chloride, sodium nitrate, potassium sulfate, at a concentration of between about 0.1 M (moles/liter)

and about 4.0 M, usually about 0.5 M to 1.5 M. The carrier fluids may be titrated or buffered to the desired pH; salts such as sodium borate, potassium phosphate, sodium phosphate, or potassium sulfate may be used depending upon the pH desired, the availability of particular salts, and compatibility of particular salts with particular carrier compounds. The salt(s) are generally present in concentrations of between about 1 mM and about 750 mM, usually between about 10 and about 500 mM, more usually between about 50 mM and 400 mM. As described above, the carrier fluids may also contain an effective amount of a suitable electrocatalyst or mediator. Carrier fluids according to the methods and apparatus of the present invention do not include an added Lewis base for axial coordination to the transition metal ion of the carrier compound.

Loader 22 is, for example, a microporous hydrophobic hollow fiber membrane array such as that which will be described more fully below in connection with FIG. 9. Suitable membrane arrays are manufactured by Bard Cardiosurgery, Inc. of Concord, Calif. These membrane arrays are typically modified to allow fluid flow both inside and outside the hollow fibers in a manner that will be apparent to those skilled in the art.

Cell 24 includes a pair of titanium or graphite current collector plates 36, 38, which press against two electrodes 40, 42. Typically, electrodes 40, 42 are carbon felt electrodes, in one example of the cell 24, having dimensions of about 2.5 cm.×10 cm.×0.5 cm. Electrodes 40, 42, and thus anode compartment 26 in cathode compartment 28, are separated by membrane 30 which is an ion permeable membrane made, for example, of Celgard or RAI anionic exchange membrane. Cell 24 is assembled in a plexiglass housing (not separately shown) having two halves which are bolted together and sealed with an O-ring or gasket seal (not shown). Cell 24 includes the necessary ports for introducing and removing carrier fluids from anode compartment 26 and cathode compartment 28. Cell 24 further includes ports for insertion of reference electrodes 44, 46 which are conveniently, but not necessarily, silver-silver chloride reference electrodes. Current collector plates 36, 38 are connected via titanium posts 48, 50 to a potentiostat (not shown) capable of supplying either a constant or variable current or voltage to cell 24. Suitable potentiostats are available, for example, from Princeton Applied Research, Princeton, N.J. Unloader 32, in the embodiment shown in FIG. 4 includes a cylindrical fluid gas separation chamber 52, equipped with a sweep gas bubbler 54 near the bottom thereof and an exit port at the top thereof. Alternatively, unloader 32 may be a hollow fiber device such as that described above in connection with loader 22.

In operation, carrier fluid is circulated through loader 22 where it is exposed, through the ligand permeable membrane, to the fluid from which oxygen is to be extracted. In the typical laboratory scale electrochemical oxygen cell 20, carrier fluid is oxygenated using air as the external fluid. The carrier fluid is circulated through anode compartment 26, where it is oxidized to dissociate bound oxygen, and then to unloader 32, where the dissociated oxygen is removed by the sweep gas or simply allowed to evolve. The deoxygenated carrier fluid is thereafter circulated through cathode compartment 28, where the carrier compound is reduced, and then back to loader 22 for repetition of the cycle.

The concentration of oxygen present in the carrier fluid is measured at several points with oxygen probes 56, 58, 60. A flow meter (not shown) is used to measure the recirculation of carrier fluid through electrochemical oxygen cell 20. In addition, the cathode and anode potentials are measured with respect to reference electrodes 44, 46, respectively, and the current through cell 24 is monitored by means that will be apparent to those skilled in the art. The flow rate of the exit gas stream is monitored as is the concentration of oxygen in the gas outlet with a fourth oxygen probe 62, so that oxygen extraction and release may be quantified. Oxygen probes 56, 58, 60, 62 are Clarke-type oxygen probes, operable to produce an electrical potential proportional to the oxygen concentration ambient to the probe. Oxygen probe 56 monitors the loading process; probe 58 monitors the oxygen evolved in anode compartment 26. Oxygen probe 60 is used to monitor the efficiency of the unloading process and unloader 32.

Preferably, the signals from oxygen probes 56, 58, 60, 62, the flow rates of the carrier fluid and the exiting gas, the potentials of the anode and cathode plates 48, 50 with respect to electrodes 44 and 46, and the current through cell 24 are all simultaneously monitored, digitized, and stored in a computer for later analysis.

Typically, this data and the carrier compound concentration, carrier fluid flow rate, and the applied cell voltages, are analyzed to derive the rate of oxygen production, the power consumed by cell 20, and the number of electrons flowing through cell 20 to produce one molecule of oxygen. Generally, it is preferred that power and the average number of electrons passed per molecule of oxygen produced should be minimized, while the rate of oxygen production should be maximized.

Results for selected cobalt carrier compounds are given in Table II. During the course of EOC experiments with Co-1,4,8,11-tetraazacyclotetradecane, a gradual degradation in performance during a 140-hour long experiment was noted, due to apparent deposition of decomposition products on current collectors 36, 38 in the EOC cell. The high electron counts observed for Co-1,4,8,12-tetraazacyclopentadecane indicate inadequate loading of the carrier compound with oxygen in loader 22. This observation was confirmed by comparison of UV-visible spectra obtained on 0.2 mM solutions of this carrier compound saturated with air and oxygen, respectively; these results showed that, due apparently to a relatively low oxygen binding constant, this carrier compound binds less oxygen than desired.

It should be noted in connection with the operation of the apparatus shown in FIGS. 2, 3, and 4 that it may prove energetically or otherwise advantageous to "cycle" only a portion of the carrier compound during any particular oxidation and/or reduction step. That is, the necessary cell voltages and energetics may be favorably adjustable by maintaining a mixture of both oxidized state and reduced state carrier compound at all times in all portions of the apparatus, so that only a portion of the carrier compound is capable of binding or binds oxygen during the complete cycle.

TABLE II

ELECTROCHEMICAL OXYGEN CELL RESULTS FOR COBALT CARRIER COMPOUNDS

| Carrier Compound | Electrocatalyst | pH | Flow[*1] (mL/min) | E, V[*2] | I, mA | EC $O_2$[*3] ml/min. | Power[*4] W/L/min. | e-/ |
|---|---|---|---|---|---|---|---|---|
| Cobalt - 1,4,8,12-Tetraaza-cyclopentadecane (4 mM) | | 7.0 | 45 | 0.5 | 300 | 0.26 | 580 | 1 |
| | | | | 0.9 | 610 | 0.96 | 573 | |
| Cobalt - 1,4,8,12-Tetraaza-cylclopentadecane (4 mM) | N,N-dimethyl-aminomethyl-ferrocene (1 mM) | 7.0 | 45 | 0.5 | 247 | 0.34 | 367 | 1 |
| Cobalt - 1,4,8,12-Tetraaza-cyclopentadecane (4 mM) | N,N,N',N'-tetra-methyldiamino-benzene (1 mM) | 7.0 | 45 | 0.5 | 322 | 0.5 | 315 | |
| Cobalt - 1,4,8,11-Tetraaza-cyclotetradecane (4 mM) | | 7.0 | 30 | 0.5 | 40 | 0.23 | 84 | |
| | | | | 0.9 | 284 | 1.5 | 159 | 2.5 |
| Cobalt - 1,4,8,11-Tetraaza-cyclotetradecane (4 mM) | N,N-dimethyl-aminomethyl-ferrocene (1 mM) | 7.0 | 30 | 0.5 | 112 | 0.45 | 126 | 3.8 |
| | | | | 0.9 | 270 | 1.6 | 151 | |

[*1] carrier fluid flow rate
[*2] applied cell potential
[*3] electrochemical oxygen production rate
[*4] power consumed, in watts/liter of $O_2$/min
[*5] electrons passed per molecule of $O_2$ produced FIG. 5 shows a schematic diagram of a working electrochemical cell and unloading station in combination with a pump for circulating the carrier and a ligand extraction station. The apparatus shown in FIG. 5 will be referred to herein as the demonstration unit. These components together form a sealed system containing a fixed volume of ligand carrier and carrier fluid. The apparatus shown in FIG. 5 is generally of a type generally intended for relatively larger scale production of oxygen. The electrochemical cell comprises twenty parallel teflon plates having sputtered gold surfaces, between which the carrier fluid is directed, in parallel. The plates are 3 mm thick and spaced at a distance of 1 mm. An individual plate is 62.5 cm long and 8 cm wide. When stacked in a parallel plate arrangement, the twenty layers have a total height of 8 cm. The use of such a bipolar cell such as this enables the use of higher voltages at proportionately smaller currents than would be required to operate a single anode, single cathode cell of the same surface area. The electrochemical cell is connected to a voltage supply capable of providing 25 amps at 2.0 volts. The unloading station comprises one or more (one is shown) hollow fiber cartridges 1 inch in diameter and 43 inches in length containing hollow fibers which consist of porous polysulfone with an interior silicon rubber skin. The surface area of the hollow fibers is 0.25 m². When more than one such cartridge is used, they are arranged for parallel flow of a commensurate fraction of the total carrier fluid flow through the apparatus. Polyvinylchloride or polypropylene piping is used to connect various inlets and outlet ports. The outlet port of the first electrode compartment is connected to the inlet port of the smaller of the two hollow fiber cartridges so that fluid which exits from the first electrode compartment enters the interior of the hollow fibers. The outlet port of this hollow fiber cartridge is connected to the inlet port of the second electrode compartment. The inlet port of the first electrode compartment is connected to the outlet port of the ligand extracting station while the outlet port of the second electrode compartment is connected through a pump to the inlet port of the ligand extracting station. In the embodiment shown, the ligand extracting station comprises one or more (one is shown) hollow fiber cartridges 3 inches in diameter and 43 inches in length, arranged for simultaneous parallel flow through the cartridges when more than one is used. Each cartridge contains 660 hollow fibers made of porous polysulfone with an interior silicon rubber skin. The hollow fibers have a membrane surface area of 2.5 m² and an interior volume of 646 ml. The space surrounding the hollow fibers is in communication with the electrochemical cell, not the interior of the hollow fibers. A fluid containing the ligand which is being extracted passes through the interior of the hollow fibers.

Operation of the demonstration unit apparatus is illustrated with the ligand carrier. Approximately 1 liter of carrier fluid is present in the interior volume of the apparatus as described above and the ligand extracting station together. Carrier fluid containing the ligand carrier having a ligand bound thereto passes from the exit port of the ligand extracting station into the inlet port of the first electrode compartment where a redox reaction takes place in order to release the ligand from the ligand carrier. Free ligand, carrier fluid, and non-binding-state ligand carrier pass from the exit port of the first electrode chamber into the ligand unloading station where ligand passes through the walls of the ligand-permeable membrane and is collected. In the particular illustration shown, oxygen passes directly into the space where it is being utilized. It is also possible to pass fluids or chemical reactants over the outside of the hollow fibers. It will of course be recognized that the ligand can be concentrated or diluted depending on the rate at which the carrier fluid is circulated. Slow circulation results in high concentrations of the ligand bound to the ligand carrier and thus released at the first electrode compartment. Carrier fluid (now depleted of ligand) and nonbinding-state ligand carrier pass from the exit port of the ligand unloading station to the inlet port of the second electrode compartment where an electrochemical reaction opposite to that which occurred in the first electrode compartment takes place. This second redox reaction reforms the original binding-state ligand carrier. Binding-state ligand carrier and carrier fluid then pass from the exit port of the electrochemical cell through a gear pump to the inlet port of the ligand extracting station. In the embodiment shown as an example in FIG. 5 which may be used to extract oxygen from water and release oxygen into a second environment, water flows through the ligand (oxygen) extracting hollow fiber cartridge at a rate of 20 gallons per minute at 20 psi pressure. Circulating carrier compound in an aqueous carrier fluid (20 mM) circulates at 0.25 gallons per minute.

The variables of operation include concentration of the carrier compound in the carrier fluid, flow rate of the carrier fluid through the apparatus, voltage applied across the electrodes, current load consumed by the electrodes, electrode area, and the volume of oxygen produced by the apparatus. When employing the ligand-metal ion carrier compounds described above, it has been found that oxidation of the carrier compounds and release of oxygen is promoted by controlling pH, usually in the range from 3 to 12, more usually in the range from 6 to 8. Typical values for these parameters are set forth in Table III below.

TABLE III

|  | Broad Range | Narrow Range |
|---|---|---|
| Carrier Compound Concentration | 1 mM–4M | 10 mM–600 mM |
| Flow Rate of Carrier Fluid | 0–$10^5$ L/min | 10 ml/min–100 L/min |
| Voltage* | 0.1–2.0 V. | 0.2–1.0 V. |
| Current Density | 100 μA–5 A/$cm^2$ | 1 mA–200 mA/$cm^2$ |
| Electrode Area | 1 $cm^2$–$10^5$ $m^2$ | 1 $cm^2$–100 $m^2$ |
| Volume $O_2$ Produced | 0.1 ml–1000 $m^3$/min | 1 ml–1000 L/min |
| pH | 3–12 | 6–8 |

*These voltage ranges apply to a cell consisting of a single anode and cathode pair. For bipolar stacks, the voltage will be proportionally higher.

A second specific embodiment designated electrochemical cell 110 of an apparatus for practicing the methods of the invention is shown schematically in FIG. 6. This electrochemical cell 110 utilizes diffusive and/or convective transport of carrier compound-ligand complexes through an electrolyte solution to transport oxygen (or other ligand) from a first fluid environment from which the ligand is extracted to a second fluid environment to which the ligand is released.

Electrochemical cell 110 includes a cathode 112, an anode 114, and an electrolyte 116 extending between cathode 112 and anode 114. Electrolyte 116 comprises a carrier fluid as described above containing a metallic complex of a polyalkylamine. Briefly, electrochemical cell 110 is operated to extract a ligand (oxygen, in this example) from a fluid (such as air, in this example) by impressing an appropriate potential across anode 112 and cathode 114 and by introducing air into a first fluid environment, e.g., chamber 118 in fluid communication with electrolyte 116 adjacent cathode 112. This fluid communication may be established, for example, with a ligand permeable membrane adjacent cathode 112 and separating electrolyte 116 from chamber 118. Alternatively, cathode 112 may be chosen to be ligand permeable and simultaneously serve as a physical separator between electrolyte 116 and chamber 118. Carrier compound, reduced at cathode 112 binds the ligand thus communicated from chamber 118. (Excess fluid may be expelled from chamber 118 via a vent 120 or the like.) The carrier compound-oxygen complex formed at cathode 112 migrates into and travels through electrolyte 116 under the influence of diffusion, convection, and/or electromigration to anode 114 where the metal of the carrier compound is electrochemically converted to its non-binding valence state and the oxygen or other bound ligand is released. Free ligand is collected in a second chamber 122 from which it is withdrawn or consumed, for example, through a vent 124. The released ligand may be diffused through a ligand-permeable membrane to second chamber 122 or an anode 114 selected to be ligand permeable, or may be removed from electrolyte 116 with a bubble dispersion device or the like, as described above.

Referring to FIG. 7, it is frequently desirable to employ a bipolar stack 150 of electrodes as the electrochemical cell of the present invention. The bipolar stack 150 includes a pair of conductor plates 152 and 154 located within a cell enclosure 156. A plurality of anodes 158 and cathodes 160 are positioned alternately between the conductive plates 150. Adjacent anode/cathode pairs 158/160 are separated by ion-permeable membranes 162, and individual anodes and cathodes may be separated by membranes 164, or may be a unitary structure having one side which functions as an anode and the other side which functions as a cathode. A voltage (or current) source 166 is connected across the conductor plates 150, and a voltage drop is induced across adjacent anode/cathode pairs 158/160. Usually, the voltage drops will be substantially equal and chosen to provide sufficient current density to evolve the desired volume of oxygen at each anode 158. With the bipolar stack 150, the total operating voltage will be greater than that for cells including a single set of one anode and one cathode. The increase will be proportional to the number of anode/cathode pairs. The current flow, however, will remain essentially the same and the overall power consumption per unit of oxygen will be the same or reduced. The advantage to using a bipolar stack is primarily that increased electrode surface areas can be obtained in a single operating unit; such a bipolar stack also may be operated at higher voltages.

The electrochemical cell compartments will contain an inlet and outlet in each anode and cathode compartment through which fluid can be conducted. Of course, one skilled in the art will recognize that anode and cathode compartments can be changed merely by reversing the electrical leads. The present example is illustrated by assuming that the first electrode compartment is an anode compartment and that an oxygen carrier which binds oxygen in the reduced state is being used. A container is attached by means of a conduit to the outlet of the anode compartment. The conduit may be a separate tube or may be formed entirely or in part from the walls of the container or the anode compartment. Since oxidation takes place in the anode compartment, the anode compartment when in operation will contain the carrier in the oxidized state and free oxygen in solution. Since all oxygen is released by the electrochemical oxidation of the carrier, an extremely high concentration of oxygen can exist in the carrier fluid. Accordingly, in embodiments in which oxygen is released to the internal environment through a ligand permeable membrane, a positive gradient across the gas permeable membrane will exist even if air is present on the opposite side of the membrane. It is only necessary that the partial pressure (chemical activity) of oxygen be lower in the internal environment than it is (locally) in the carrier fluid. This is the meaning of "low partial pressure" of the ligand as used in this application in reference to the environment in which the ligand is being released.

The fluid is then transported through a second conduit attached to the container so that fluid which enters the container from the anode compartment contacts the membrane prior to exiting the container through the second conduit. This second conduit is attached to an inlet in the cathode compartment and can be formed in the same manner as the first conduit described above. The cathode compartment also contains an outlet through which the fluid passes on its way to pick up oxygen from the environment.

To continue the illustration of releasing oxygen, where oxygen is generally being produced for consumption, it is relatively easy to maintain a low partial pressure of oxygen on the gas-collecting side of the container membrane. If this oxygen is consumed by a human, animal, or fuel burning engine, the result is the same: reduction of the partial pressure of oxygen on the oxygen consuming side of the membrane, which maintains the pressure gradient and the high rate of oxygen removal from the system.

Of course, it is possible to consume the oxygen without isolating the oxygen in gaseous form. Oxygen in the carrier fluid may be transported to a fuel cell where the oxygen is consumed directly. In a preferred embodiment of the invention, the anode compartment is itself part of the cathode portion of an energy generating fuel cell as well as being a place where oxygen is released from the carrier so that no transportation is required. Fuel cells are of course well known and can easily be adapted to the process of the present invention. See, for example, U.S. Pat. Nos. 4,215,182; 4,075,396; and McDougall, *Fuel Cells*, John Wiley and Sons, New York (1976).

In some embodiments, it may be possible and desirable to unload the oxygen from the carrier compound by transporting the oxygen-bound carrier compound in the carrier fluid to an unloading compartment in which the oxygen is removed by exposing the carrier fluid to a sufficiently low pressure (partial pressure) of oxygen to deplete the carrier fluid of oxygen, without electrochemical release of the bound oxygen.

When a ligand other than oxygen is being collected at the unloading station, other means of maintaining a low ligand partial pressure (or concentration when the ligand is nonvolatile and is being extracted into a liquid phase) will be required. Generally, some chemical reaction which converts the ligand to a state not free to migrate back into the carrier fluid will be used, or the ligand will be transported away from the membrane by physical means. Chemical reactions for removing ligands (e.g., NO in a waste stream) are already known. The present invention offers advantages over direct contact of a waste stream with these chemical reactants. If the ligand being removed from a waste stream is present only in small quantities, it is possible to concentrate the ligand by utilizing the binding affinity of the ligand carrier and to release the ligand in high concentration for ready reaction with the ultimate removing chemical. The method of the invention also provides a method for readily concentrating minute quantities of material which are to be removed by physical transport; e.g., trapping as a compressed gas or concentrated solution for later disposal.

One component of an apparatus of the present invention is the ligand permeable membrane. However, the technology relating to the production and use of ligand permeable membranes is well known and need not be set forth here in detail. See, for example, "Membrane Technology", Kirk-Othmer *Encyclopedia of Chemical Technology*, 3rd Edition, John Wiley and Sons, New York, Volume 15, pages 92-131, and the references cited therein. Certain preferred embodiments of suitable membranes are discussed here, however, in order to exemplify the invention.

The selection of a membrane for use in the present invention is not limited other than by the ability of the membrane to pass the ligand while retarding the passage of other components of the fluid environment from which the ligand is being extracted. It will be desirable to select a membrane based on the purpose for which it will be used, e.g., use in contact with exhaust gas or extraction of a ligand from a waste liquid stream. Most important synthetic membranes are formed from organic polymers, and there are extensive tabulations of permeability coefficients for various ligand/polymer systems now in existence. See, for example, van Amerongen, *Rubber Chem. Technol.*, 37 1065 (1964); Allen et al, *J. Member. Sci.*, 2.153 (1977); Yasuda et al in Brandrup et al Eds., *Polymer Handbook*, Second Edition, John Wiley and Sons, New York, 1975, p. 111; and Bixlar et al in Sweeting, Ed., *The Science and Technology of Polymer Films*, Vol. II, John Wiley and Sons, New York, 1971, p. 85. In addition to ligand permeability, inertness to the external fluid environment and the internal carrier fluid are also required.

The physical microstructure of the membrane is not important so long as the membrane performs the function described herein. Accordingly, dense films, porous membranes, and asymmetric and composite membranes are suitable. The macroscopic form of the membrane is also relatively unimportant although hollow fibers are preferred over flat sheets or tubular membrane configurations since hollow fibers are self-supporting and thus eliminate the need for expensive support materials. In fact, hollow fiber cartridges in which a plurality of gas permeable hollow fibers are connected in parallel between two manifolds at opposite ends of each tube can readily be adapted for use in the present invention. For example, Romicon manufactures a hollow fiber cartridge 3 inches in diameter and 43 inches long containing 660 hollow fibers joined to manifolds at opposite ends of the cartridge. The hollow fibers have a surface area of 2.5 $m^2$ and volume of 647 ml and are in the form of a polysulfone membrane with a silicone rubber layer over the polysulfone layer to form a composite membrane. Fluid from the environment, e.g. seawater, is transported through the inside the hollow fibers (i.e., the interior of the fibers is the outside of the closed container) where extraction of oxygen into the fluid carrier takes place. When used to release oxygen, for example, the cartridge walls form an oxygen-collecting chamber around the hollow fibers through which the carrier fluid is transported.

When the environmental fluid from which oxygen is extracted is an aqueous fluid, a polymer having a high permeability to oxygen is particularly preferred because of the low chemical activity of oxygen in water. Silicone rubber, natural rubber, poly(phenylene oxide), and poly(trimethylsilylpropyne), often abbreviated as PMSP, have been found to form suitable membranes in such environments. When oxygen is being extracted from air, high permeability is less important. In any event, the present invention has advantages over passive diffusion systems since the partial pressure of oxygen in the carrier fluid itself is essentially zero at all times until the oxygen binding compound is saturated. Accordingly, a constant oxygen chemical activity gradient across the membrane exists in practice since the oxygen bound to the carrier compound will normally be transported to a second location where the oxygen will be unloaded prior to saturation.

Another material of interest is porous polysulfone in the form of hollow fibers having an internal skin of silicone (e.g., polydimethylsiloxane). This composite material provides both strength and high oxygen transport. Composite fibers consisting of a porous outer layer and an oxygen permeable layer (here permeable is used in the traditional sense of transport by solution of oxygen in the membrane) on the inside of the fiber are preferred for use in extracting oxygen from fluids under pressure, such as seawater. Hollow fibers having interior diameters of 50 microns have been produced as have much larger hollow fibers having interior diameters of 2 millimeters. Smaller fibers have a greater resistance to pressure, with bursting strengths of 6.000 pounds per square inch having been recorded. In lower pressure environments or when extracting oxygen from air, large diameter fibers are preferred since the larger fibers are rated up to 50 pounds per square inch bursting pressure and offer less resistance to flow, thereby reducing energy required to drive water or air through the fibers where extraction takes place. This is particularly true when large volumes of oxygen are desired to be extracted since a theoretical oxygen extraction of 1 liter per second requires that 3175 gallons of, e.g., seawater must contact the membrane surface each minute. Efficiencies of extracting oxygen across membranes of 85% have been obtained in practice.

Preferred membranes of the invention, particularly those intended for use in an aqueous environment, should in addition have minimal water and carrier fluid flux. Typically, water flux through the membrane is limited by selecting hydrophobic membranes, such as fluorocarbons.

During operation, flow of carrier in contact with the second side of the membrane is balanced against oxygen flux which in turn depends on the oxygen concentration in the environment from which oxygen is being extracted and the rate at which this environment contacts the membrane. Higher oxygen carrier concentrations and faster carrier flow rates both operate to increase the rate of oxygen pick-up. High capacity oxygen carriers are therefore preferred since they decrease the required volume of carrier and minimize pumping requirements.

Loading and unloading devices can be, as discussed above, hollow fiber devices, but are not so limited. In addition, other continuous aeration or gas exchange devices may be used, including plate or packed gas-liquid contacting columns, bubble dispersion devices and the like, as discussed for example in Section 18 of the *Chemical Engineers' Handbook*, Perry and Chilton, eds., 5th Ed., 1973.

The individual components of an electrochemical cell used in the practice of the method of the invention are readily available to those skilled in the art although certain combinations of these components have not been previously known. For example, the electrochemical reactions themselves can be conducted in any electrochemical cell which has an anode compartment and a cathode compartment through which the appropriate fluids can be transported. For simplicity in the following discussion, it will be assumed that an oxygen carrier in which the oxygen binding state is a lower oxidation state and the nonbinding state is a higher oxidation state is being used in order to simplify discussion of anode and cathode compartments. However, it will be easily recognized that when an oxygen carrier in which the oxygen binding state is a higher oxidation state can readily be used by reversing the anode and cathode.

Although the design of the electrode and cathode compartments of the electrochemical cell are not critical to the practice of this invention, certain embodiments are preferred. For example, a parallel plate electrochemical cell in which anode and cathode compartments alternate (as described above in connection with FIG. 7) in order to increase voltage and decrease current is a preferred embodiment. In order to maximize contact of the carrier fluid containing the oxygen binding compound with the anode and cathode, it is preferred that the anode and cathode compartments have a thickness of no more than 5 millimeters, preferably no more than 1 millimeter. Particularly preferred are porous electrodes, such as vitreous carbon, carbon felt, or polytetrafluoroethylene covered with a thin layer of an inert metal such as gold or platinum. The carrier fluid in such an embodiment passes through the porous electrodes, the spaces of which form the anode and cathode compartments.

The electrode material will usually be a metal or a carbon/graphite, with suitable metals including transition metals such as titanium, iron, nickel, copper, silver, platinum, gold, palladium, tin, tantalum, cobalt, ruthenium oxide, lead, cadmium, and alloys and mixtures thereof. Suitable carbon/graphite electrodes include glassy (amorphous) carbons, reticulated vitreous carbons, pyrolytic carbons, carbon felts, and the like.

The construction of the electrode will depend on the material type, with metal electrodes generally being in the form of plates, bars, and screens, or being sintered to form a highly porous structure. Metal electrodes may also be formed by depositing a film or layer of the metal on a nonconductive substrate, such as glass. The structure of carbon/graphite electrodes will depend upon the type of carbon. Glassy carbon electrodes are generally flat, polished surfaces while reticulated vitreous carbons are glass-like porous structures, typically pyrolyzed polyacrylonitriles. Pyrolytic carbons are produced by vapor phase deposition of carbon on a substrate, resulting in a polycrystalline structure with a high degree of atomic orientation.

The apparatus and method of the invention can be used in any application where it is desirable to remove oxygen from one location and concentrate it in a second location. For example, there are many applications in which the oxygen is present as a contaminant in a fluid, and removal of oxygen therefrom is desired. For example, oxygen degrades food products such as beer, wine, and orange juice, and removal of oxygen from these fluids greatly enhances the shelf storage life of the commodity.

In other applications, it is desirable to increase the concentration of oxygen above that which is present in a given environment. For example, persons afflicted with lung disorders who require a high concentration of oxygen for ease of breathing are now mostly limited to bottled oxygen, and movement of such persons is accordingly severely restricted. Miners also need higher oxygen levels than are available under some mining conditions.

Oxygen may also be extracted from water using the apparatus and method of the invention. Typical applications include supplying oxygen to free-swimming divers, to divers in submersible vehicles, to fuel cells which operate under water, and to various energy consuming engines which require oxygen for combustion processes.

While the above is a complete description of the preferred embodiments of the invention, other arrangements and equivalents are possible and may be employed without departing from the true spirit and scope of the invention. Therefore the description and illustrations should not be construed as limiting the scope of the invention, which is delineated by the appended claims.

We claim:

1. A method for extracting a ligand from a first fluid environment, the method comprising the steps of:

contacting the first fluid environment containing ligand with a first surface of a first ligand permeable membrane having a first surface and a second surface wherein the membrane separates the environment from an interior space of a container;

contacting a carrier fluid with the second surface of the membrane wherein the carrier fluid is confined in the container and the carrier fluid contains a carrier compound, whereby at least a portion of a ligand which diffuses through the membrane binds to the carrier compound to give bound ligand complex;

transporting the carrier fluid containing the bound ligand complex to a first electrode compartment of an electrochemical cell which forms a second portion of the container;

electrochemically modulating the carrier compound to an oxidation state having a relatively less binding affinity for the ligand, thereby releasing free ligand into the carrier fluid and producing a non-binding state carrier compound;

removing ligand from the carrier fluid to give a ligand depleted carrier fluid;

transporting the ligand depleted carrier fluid containing the non-binding state carrier compound to a second electrode compartment of an electrochemical cell which forms a third portion of the container; and electrochemically modifying the non-binding state carrier compound to reform the binding state carrier compound;

wherein the carrier compound comprises a metallic complex of a transition metal ion and a macrocyclic amine having the general formula:

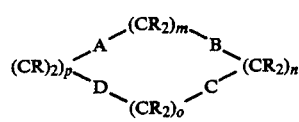

or:

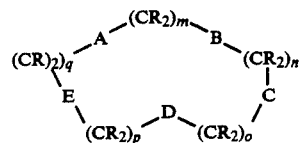

or:

-continued

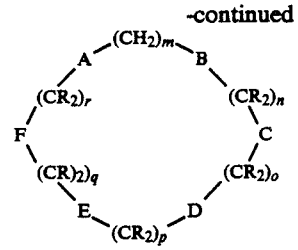

where:
A, B, C, D, E, and F are each nitrogen, oxygen, sulfur, or phosphorous;
m, n, o, p, q, and r are each 2, 3, 4, 5 or 6; and
each R is selected from the group consisting of hydrogen, short chain linear alkyl, and short chain branched alkyl, or $R_2$ is ketyl.

2. The method of claim 1 wherein the carrier compound comprises a metallic complex of a macrocyclic amine having the general formula:

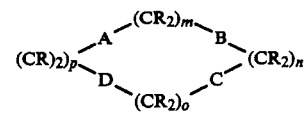

where:
at least three of A, B, C, and D are each nitrogen, the remaining one of A, B, C, and D being nitrogen, oxygen, sulfur, or phosphorous; and
m, n, o, and p are each 2, 3, or 4.

3. The method of claim 2 wherein A, B, C, and D are each nitrogen and wherein at least two of m, n, o, and p are equal to 3, the remaining ones of m, n, o, and p being equal to 2.

4. The method of claims 1, 2, 3, or 4 using an electrocatalyst to transfer electrons between the electrodes and the carrier compound, the electrocatalyst being mobile in the carrier fluid.

5. The method of claim 4 wherein the electrocatalyst is selected from the group consisting of substituted ferrocenes and substituted phenylenediamines.

6. The method of claim 1 wherein at least one of A, B, C, D, and E is nitrogen from a heterocyclic aromatic amine.

7. The method of claim 1 wherein the transition metal ion is selected from the group consisting of manganese, ion, cobalt, copper, and nickel.

8. The method of claim 7 wherein the metal is cobalt.

9. A method for extracting a ligand from a first fluid environment and releasing the ligand to a second fluid environment, the method comprising the steps of:

providing an electrochemical cell including an anode, a cathode and an electrolyte comprising a transition metal carrier compound having the general formula:

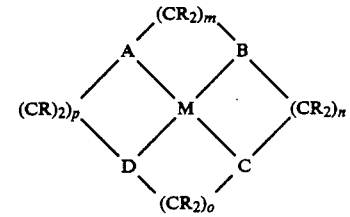

-continued or:

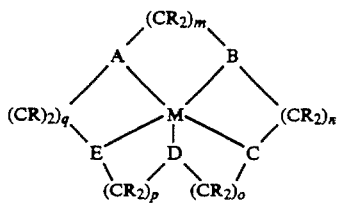

or:

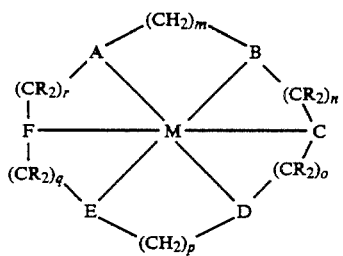

where:
A, B, C, D, E, and F are each nitrogen, oxygen, sulfur, or phosphorous, m, n, o, p, q and r are each 2, 3, 4, 5 or 6, each R is selected from the group consisting of hydrogen, short chain linear alkyl, and short chain branched alkyl, or $R_2$ taken together is ketyl, and M is a transition metal ion;

providing a potential across the cell sufficient to convert the metal of the carrier compound to a binding valence state at the cathode and convert, at the anode, the metal of a carrier compound ligand complex to a non-binding valence state;

communicating the ligand from the first fluid environment to the electrolyte in the region of the cathode so that the carrier compound ligand complex is formed between the ligand and the binding valence state carrier compound; and transporting the carrier compound ligand complex to the anode for release of the ligand.

10. The method of claim 9 further comprising the step of electrochemically releasing the ligand from the carrier compound ligand complex to the second fluid environment.

11. The method of claim 9 wherein the metal is selected from the group consisting of manganese, iron, cobalt, copper, and nickel.

12. The method of claim 9 using an electrocatalyst to transfer electrons between the electrodes and the carrier compound the electrocatalyst being mobile in the carrier fluid, covalently linked to the carrier compound, immobilized on at least one of the electrodes, or immobilized on a substrate other than an electrode and circulated between the electrodes.

13. The method of claim 12 wherein the electrocatalyst is mobile in the carrier fluid and is selected from the group consisting of substituted ferrocenes and substituted phenylenediamines.

14. A method as in claim 12, wherein a voltage is applied across the electrodes, said voltage being from about 0.1 to 0.5 volts less than that applied under the conditions of the cell in the absence of the electrocatalyst.

15. An electrochemical system for extracting molecular oxygen from a fluid mixture feedstock, said system comprising:

an oxygen loading station;

an electrochemical cell including a pair of electrodes;

a voltage source connected to the electrodes;

a carrier fluid which circulates between the electrodes of the electrochemical cell and the oxygen loading station, said carrier fluid including a carrier compound capable in a first oxidation state of binding molecular oxygen and in a second oxidation state of releasing bound oxygen; and an electrocatalyst in proximity to at least one of the electrodes, said electrocatalyst selected to promote electron transfer between the electrode and the carrier compound;

wherein the carrier compound is a transition metal complex having the general formula:

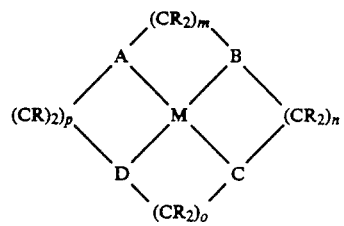

or:

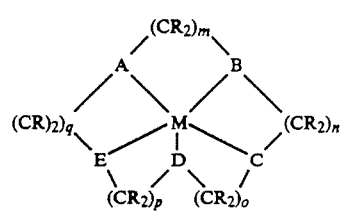

or:

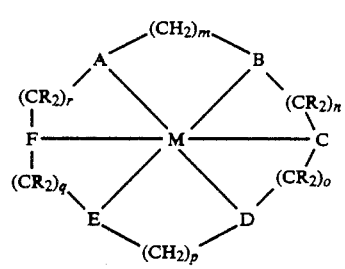

where:
A, B, C, D, E, and F are each nitrogen, oxygen, sulfur, or phosphorous;

m, n, o, p, q, and r are each 2, 3, 4, 5 or 6;

each R is selected from the group consisting of hydrogen, short chain linear alkyl, and short chain branched alkyl or $R_2$ taken together is ketyl; and M is a transition metal ion.

16. The system of claim 15 wherein the carrier compound is a transition metal complex having the general formula:

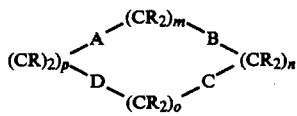

where:
- at least two of A, B, C, and D are nitrogen, the remaining ones of A, B, C, and D being nitrogen, oxygen, sulfur, or phosphorous;
- m, n, o, and p are each 2, 3, or 4; and
- M is a transition metal ion selected from the group consisting of manganese, iron, cobalt, nickel, and copper ions.

17. A composition of matter for use in electrochemical ligand extraction and generation processes comprising:
an aqueous solution of greater than about 10 millimoles per liter of a metallic complex of a transition metal ion and a macrocyclic amine having the general formula:

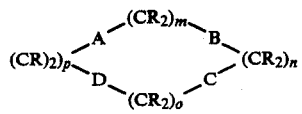

or:

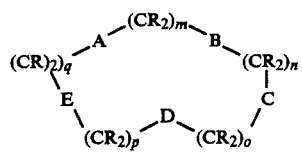

or:

-continued

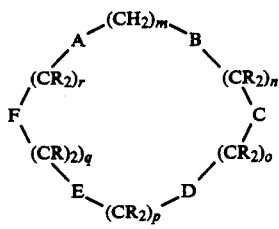

where:
- A, B, C, D, E, and F are each nitrogen, oxygen, sulfur, or phosphorous;
- m, n, o, p, q, and r are each 2, 3, 4, 5 and 6;
- each R is selected from the group consisting of hydrogen, short chain linear alkyl, and short chain branched alkyl, or $R_2$ is ketyl; and
- the transition metal ion is selected from the group consisting of manganese, iron, cobalt, nickel, and copper ions.

18. The composition of matter according to claim 17 further comprising a supporting electrolyte including a salt selected from the group consisting of sodium chloride, potassium chloride, sodium nitrate, and potassium nitrate, the salt having a concentration between about 0.1 and about 3.0 molar.

19. The composition of matter according to claim 17, titrated to a pH of about 1 pH unit above the pH at which greater than about 50% of the metallic complex, when exposed to an oxygen containing environment, is present as an oxygen complex.

20. The composition of matter as in claim 17, wherein the carrier fluid is at a pH in the range from about 5 to 9 and further comprising an electrocatalyst, present at a concentration from about 0.01 mM to 1 M, selected from the group consisting of substituted ferrocenes and substituted phenylenediamines.

* * * * *

UNITED STATES PATENT AND TRADEMARK OFFICE
CERTIFICATE OF CORRECTION

PATENT NO.   :   4,952,289
DATED        :   August 28, 1990
INVENTOR(S)  :   Joseph P. Ciccone et al.

It is certified that error appears in the above—identified patent and that said Letters Patent is hereby corrected as shown below:

Column 1, after the title, please insert the following paragraph:

--This invention was made with Government support under contract N00014-85-C-0317 awarded by the Department of the Navy. The Government has certain rights in the invention.--

Signed and Sealed this

Tenth Day of August, 1993

Attest:

MICHAEL K. KIRK

*Attesting Officer*  *Acting Commissioner of Patents and Trademarks*